(12) United States Patent
Nanchahal et al.

(10) Patent No.: US 10,669,334 B2
(45) Date of Patent: *Jun. 2, 2020

(54) TREATMENT FOR DUPUYTREN'S DISEASE

(71) Applicant: Oxford University Innovation Limited, Oxford (GB)

(72) Inventors: Jagdeep Nanchahal, Richmond Surrey (GB); Kim Suzanne Midwood, London (GB)

(73) Assignee: Oxford University Innovation Limited, Oxford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/399,547

(22) Filed: Apr. 30, 2019

(65) Prior Publication Data

US 2019/0322733 A1     Oct. 24, 2019

Related U.S. Application Data

(63) Continuation of application No. 14/852,442, filed on Sep. 11, 2015, now Pat. No. 10,273,296, which is a continuation of application No. 13/882,262, filed as application No. PCT/EP2011/069147 on Oct. 31, 2011, now Pat. No. 9,138,458.

(30) Foreign Application Priority Data

| Oct. 30, 2010 | (GB) | ................................. | 1018325.9 |
| Nov. 1, 2010 | (GB) | ................................. | 1018362.2 |
| Aug. 10, 2011 | (GB) | ................................. | 1113716.9 |

(51) Int. Cl.
| C07K 16/24 | (2006.01) |
| A61K 9/00 | (2006.01) |
| A61K 9/06 | (2006.01) |
| A61K 9/08 | (2006.01) |
| A61K 31/00 | (2006.01) |
| A61K 45/06 | (2006.01) |
| A61K 38/17 | (2006.01) |
| A61K 38/00 | (2006.01) |

(52) U.S. Cl.
CPC .......... *C07K 16/241* (2013.01); *A61K 9/0014* (2013.01); *A61K 9/0019* (2013.01); *A61K 9/06* (2013.01); *A61K 9/08* (2013.01); *A61K 31/00* (2013.01); *A61K 38/1709* (2013.01); *A61K 45/06* (2013.01); *A61K 38/00* (2013.01); *C07K 2317/21* (2013.01); *C07K 2317/24* (2013.01); *C07K 2317/55* (2013.01); *C07K 2317/76* (2013.01); *C07K 2319/30* (2013.01)

(58) Field of Classification Search
None
See application file for complete search history.

(56) References Cited

U.S. PATENT DOCUMENTS

| 5,589,171 | A | 12/1996 | Wegman |
| 5,656,272 | A | 8/1997 | Le et al. |
| 6,031,005 | A | 2/2000 | Easterling |
| 6,060,474 | A | 5/2000 | Williams et al. |
| 6,086,872 | A | 7/2000 | Wegman et al. |
| 6,090,382 | A | 7/2000 | Salfeld et al. |
| 6,353,028 | B2 | 3/2002 | Easterling |
| RE39,941 | E | 12/2007 | Wegman |
| 7,431,927 | B2 | 10/2008 | Couto et al. |
| 7,553,488 | B2 | 6/2009 | Tessier et al. |
| 8,063,182 | B1 | 11/2011 | Brockhaus et al. |
| 9,138,458 | B2 | 9/2015 | Nanchahal |
| 10,273,296 | B2 * | 4/2019 | Nanchahal ........... A61K 9/0014 |
| 2001/0056079 | A1 | 12/2001 | Hansson |
| 2004/0161761 | A1 | 8/2004 | Ferguson et al. |
| 2006/0216293 | A1 | 9/2006 | Couto et al. |
| 2008/0025986 | A1 | 1/2008 | Ozes et al. |
| 2009/0203632 | A1 | 8/2009 | Avelar et al. |

FOREIGN PATENT DOCUMENTS

| GB | 2 323 530 A | 9/1998 |
| WO | WO 02/074337 A1 | 9/2002 |
| WO | WO 2004/082705 A1 | 9/2004 |
| WO | WO 2005/074913 A2 | 8/2005 |
| WO | WO 2010/102262 A1 | 9/2010 |

OTHER PUBLICATIONS

International Search Report for PCT/EP2011/069147.
Badalamente, Marie A., et al., "Efficacy and Safety of Injectable Mixed Collagenase Subtypes in the Treatment of Dupuytren's Contracture," The Journal of Hand Surgery, vol. 32A, No. 6, (Jul.-Aug. 2007), pp. 767-774.
Goldberg, Mytien T., et al., "TNF-α Suppresses α-Smooth Muscle Actin Expression in Human Dermal Fibroblasts: An Implication for Abnormal Wound Healing," Journal of Investigative Dermatology, vol. 127, (2007), pp. 2645-2655.
Halayko, Andrew J., et al., "S100A89/A9: a mediator of severe asthma pathogenesis and morbidity?," Canadian Journal of Physiology and Pharmacology, 87, (2009), pp. 743-755.
Hurst, Lawrence C., et al., "Injectable Collagenase Clostridium Histolyticum for Dupuytren's Contracture," The New England Journal of Medicine, 361 (10), (Sep. 3, 2009), pp. 968-979.
Khanna, Dinesh, et al., "Infliximab may be effective in the treatment of teroid-resistant eosinophilic fasciitis: repot of three cases," Rheumatology, Oxford University Press, vol. 49, No. 6 (Jun. 1, 2010), pp. 1184-1188.
Krishnaswamy, Guha, et al., "The Human Mast Cell," Methods in Molecular Biology, vol. 315, (2006), pp. 13-34.

(Continued)

*Primary Examiner* — Blaine Lankford
(74) *Attorney, Agent, or Firm* — John P. White; Cooper & Dunham LLP

(57) ABSTRACT

Musculoskeletal fibroproliferative disorders, such as Dupuytren's disease may be treated by administering locally a TNF-α antagonist. TNF-α antagonists find particular utility in inhibiting the progression of early disease state Dupuytren's disease and other musculoskeletal fibroproliferative disorders and, in combination with extracellular matrix degradation agents (such as collagenase or matrix metalloproteinase I), treating advanced disease state Dupuytren's disease and, in particular inhibiting recurrence.

11 Claims, 17 Drawing Sheets

(56) References Cited

OTHER PUBLICATIONS

Liu, Hui, et al., "[Effect of inhibitors of signal transducer and activator of transcription-1/3 on expression of tumor necrosis factor-alpha induced by high mobility group box-1 protein inflammatory response in rat peritoneal macrophages]," U.S. National Library of Medicine, [Online], (Feb. 1, 2006), abstract.

Pilcher, B., et al., "Alpha Smooth Muscle Actin is Expressed by Myofibroblasts During Dupuytren's Disease," Anatomical Record, vol. 229, No. 4, (Jan. 1, 1991), p. 70A.

Rombouts, Jean-Jacques MD, et al., "Prediction of recurrence in the treatment of Dupuytren's disease: Evaluation of a histologic classification," The Journal of Hand Surgery, vol. 14A, No. 4, (Jul. 1989), pp. 644-652.

Uribarri, Jaime, et al., "Diet-Derived Advanced Glycation End Products Are Major Contributors to the Body's AGE Pool and Induce Inflammation in Healthy Subjects," Ann. N.Y. Acad. Sci., 1043, (2005), pp. 461-466.

Verjee, Liaquat Suleman, et al., "Myofobroblast Distribution in Dupuytren's Cords: Correlation with Digital Contracture," JHS, vol. 34A, (Dec. 2009), pp. 1785-1794.

Verjee, Liaquat Suleman, et al., "Post-Transcriptional Regulation of α-Smooth Muscle Actin Determines of the Contractile Phenotype of Dupuytren's Nodular Cells," Journal of Cellular Physiology, vol. 224 (3), (2010), pp. 681-690.

Yuan Zhiqiang, et al., "Construction and characterization of the HMGB1 mutant as a competitive antagonist to HMGB1 induced cytokines release," Biochemical and biophysical Research Communications, vol. 372, No. 4, (Aug. 8, 2008), pp. 703-707.

\* cited by examiner

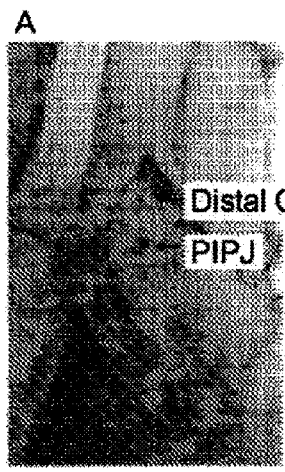 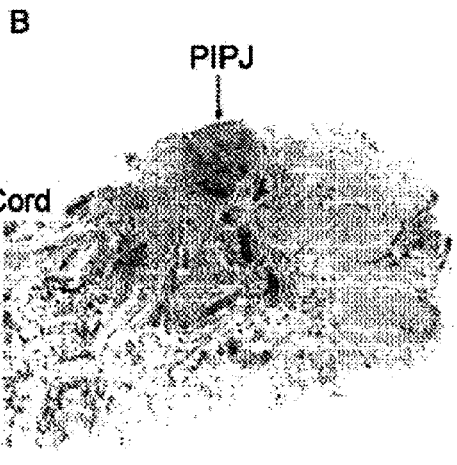 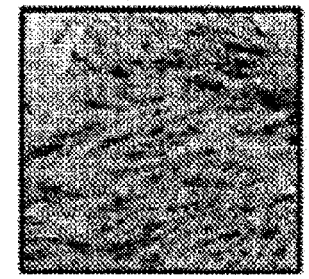
Figure 1A  Figure 1B
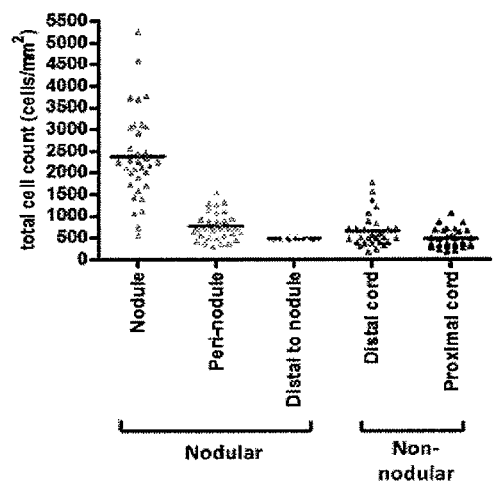 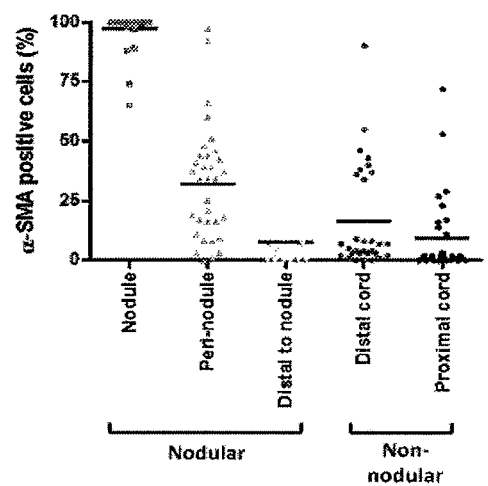
Figure 2A  Figure 2B

Figure 3A          Figure 3B
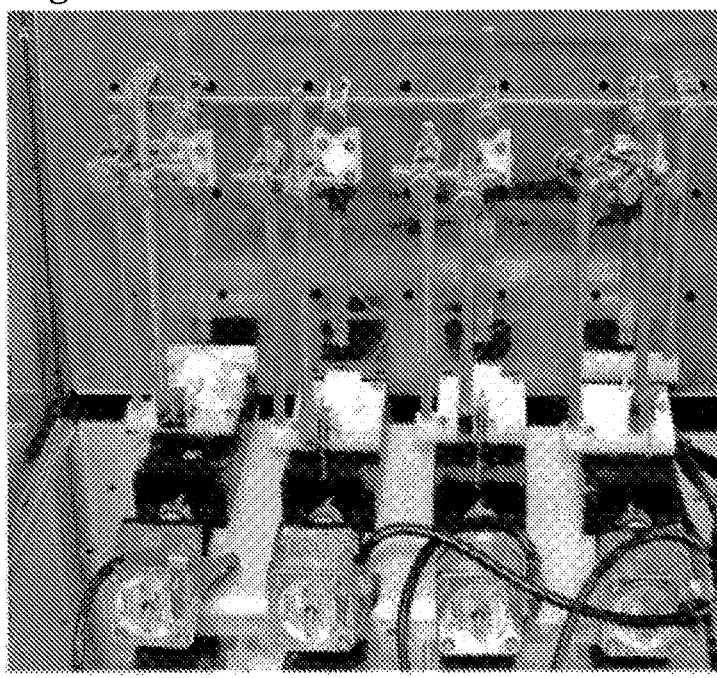
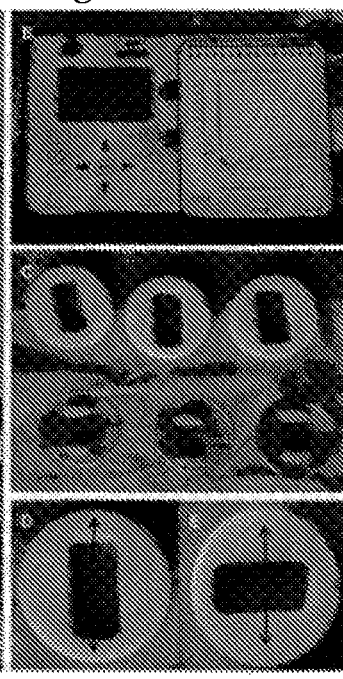
Figure 3D    Figure 3E
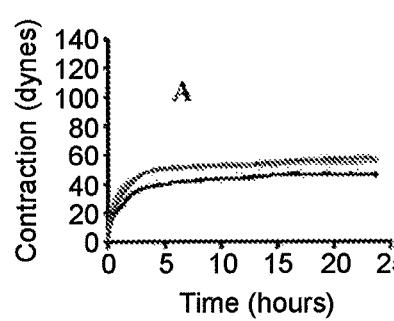
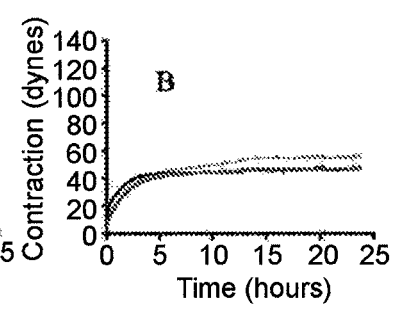
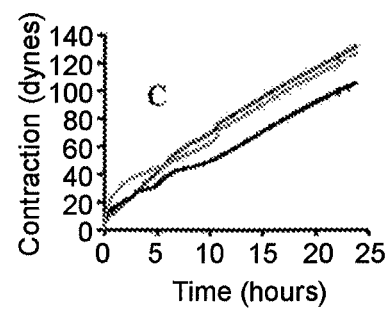
Figure 4A          Figure 4B          Figure 4C

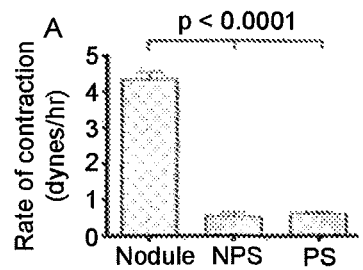
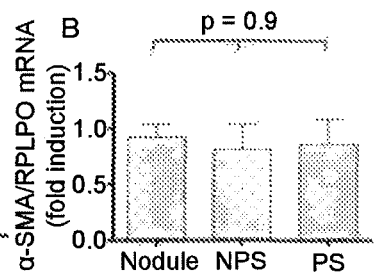
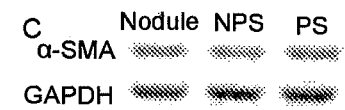
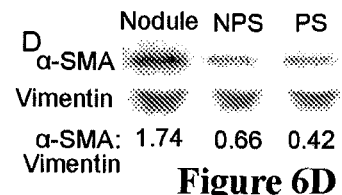
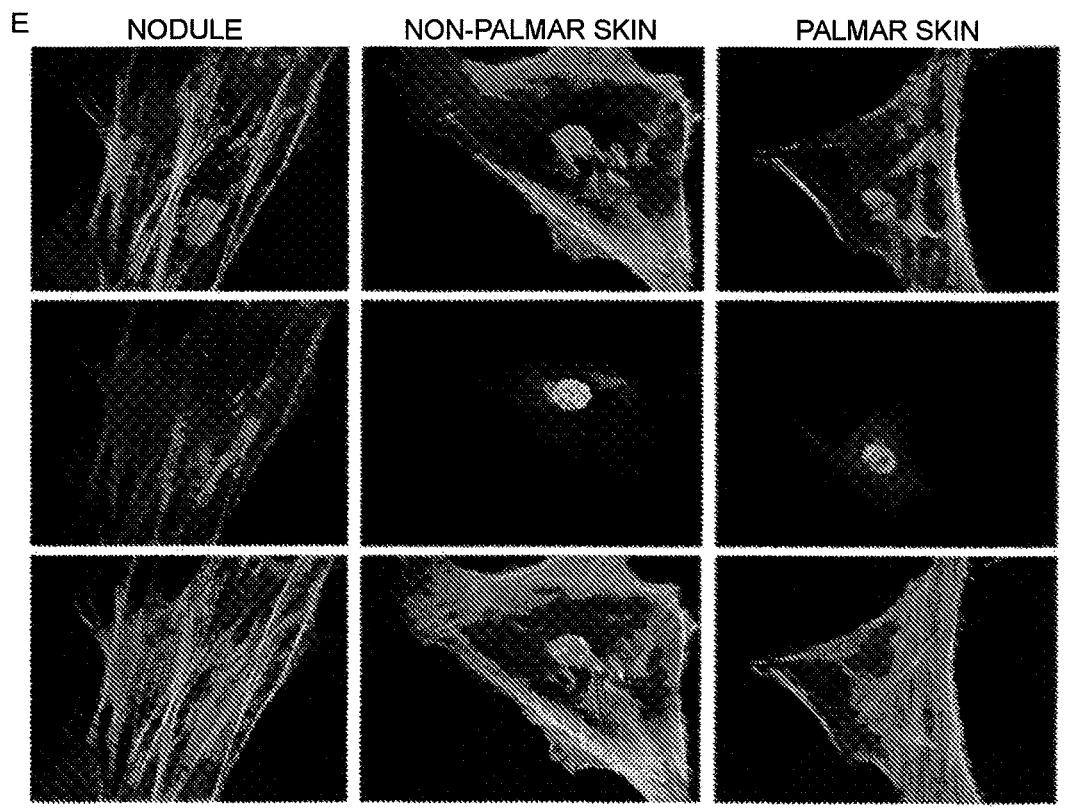
Figure 6E

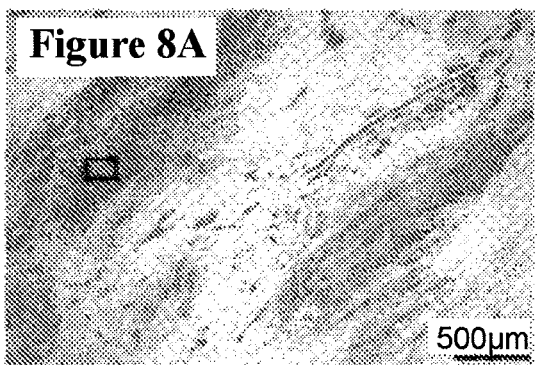
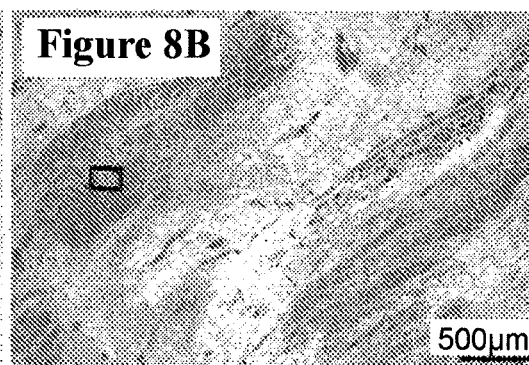
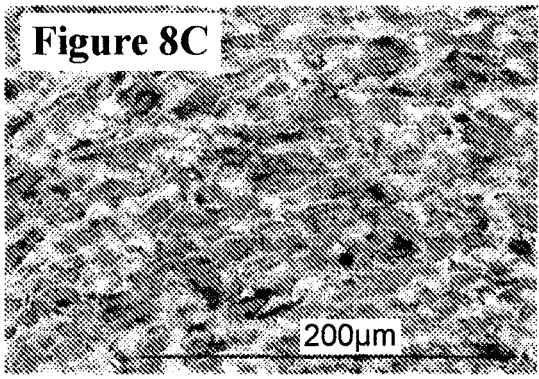
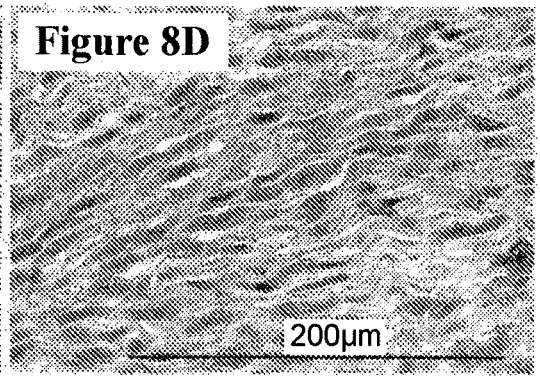

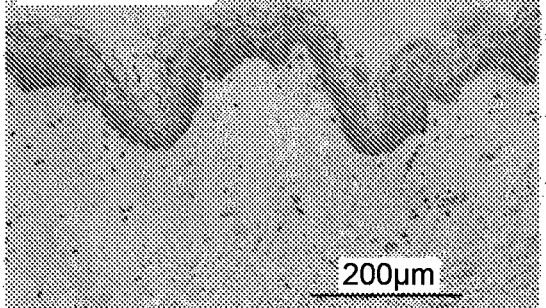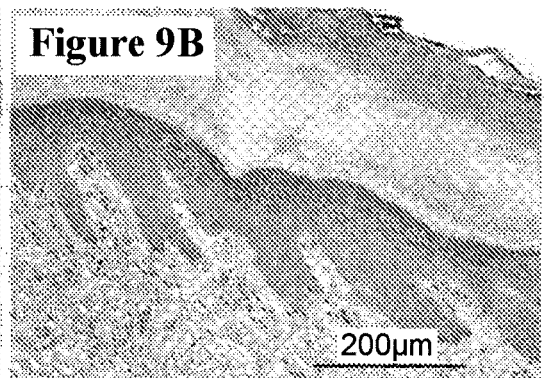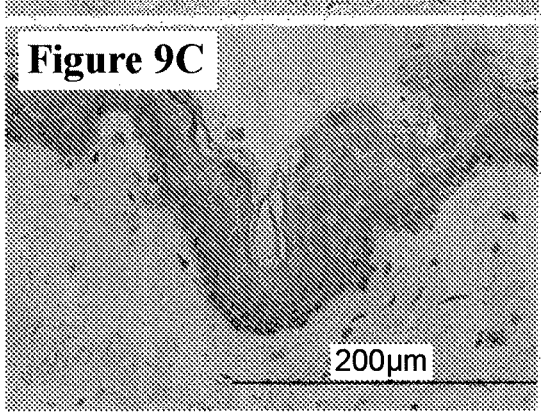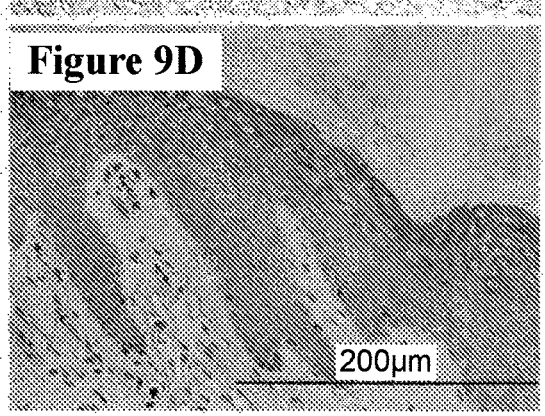

TREATMENT FOR DUPUYTREN'S DISEASE

This application is a continuation of U.S. application Ser. No. 14/852,442, filed Sep. 11, 2015, now allowed, which is a continuation of U.S. application Ser. No. 13/882,262 filed Jul. 16, 2013, now U.S. Pat. No. 9,138,458, issued Sep. 22, 2015, which is a § 371 national stage of PCT/EP2011/069,147, filed Oct. 31, 2011, claiming priority of GB 1113718.9, filed Aug. 10, 2011; GB 1018362.2, filed Nov. 1, 2010; and GB 1018325.9, filed Oct. 30, 2010, the contents of each of which are incorporated by reference herein in their entirety.

FIELD OF THE INVENTION

This invention relates to the treatment of musculoskeletal fibroproliferative disorders such as fibromatosis and, in particular, Dupuytren's disease. In particular it relates to a composition or therapeutic agent or to a combination of such compositions or therapeutic agents for the treatment, prophylaxis or prevention of progression of musculoskeletal fibroproliferative disorders, especially Dupuytren's disease, to the use of such composition/therapeutic agent or combination of compositions/therapeutic agents for the treatment, prophylaxis or prevention of progression of musculoskeletal fibroproliferative disorders, especially Dupuytren's disease and to a method of treating musculoskeletal fibroproliferative disorders, especially Dupuytren's disease.

BACKGROUND OF THE INVENTION

Dupuytren's disease, which is alternatively known as palmar fibromatosis (or in its established disease state Dupuytren's contracture), is a disease associated with the build up of extracellular matrix materials such as collagen on the connective tissue of the hand (the palmar fascia) causing it to thicken and shorten with the physical effect of causing the fingers to curl, most commonly the ring finger and little finger.

Dupuytren's disease affects approximately 5% of the white Caucasian population. The commonest manifestation is progressive flexion contracture of the digits of the hand, resulting in significantly compromised function. It affects both males and females, but the incidence is higher in males.

The causes of Dupuytren's disease are not well understood and underlying disease is not currently curable.

Treatment of Dupuytren's disease has traditionally been invasive surgical techniques. Primarily, the treatment has involved surgical excision of the offending tissue. In severe or recurrent disease, the surgical excision may be combined with excision of the overlying palmar skin and resurfacing of the cutaneous defect with full-thickness skin graft. Surgery is typically followed by prolonged rehabilitation, usually lasting 3 months and complications have been reported in up to 20% of cases. Such surgical correction is the mainstay treatment of later stage disease when secondary changes to tendons and joints have developed. A less invasive surgical intervention is needle fasciotomy in which the fibrous bands (contractures) in connective tissue are divided using the bevel of a needle.

Enzymatic cleavage of the affected tissue has been the focus of development to reduce invasiveness associated with surgery and improve recovery time. This approach has led to trials of collagenase. A bacterial collagenase, Clostridial collagenase, has been granted FDA approval as Xiaflex™ to Pfizer and Auxilium. USRE39941, U.S. Pat. Nos. 5,589,171 and 6,086,872 describe the use of bacterial collagenase for the enzymatic cleavage of connective tissue in the treatment of Dupuytren's disease. Bacterial collagenases suffer from certain disadvantages: for example lack non-selective cleaving of various collagen materials including collagen type IV associated with blood vessels; and, in the case of Xiaflex™, possible allergic reactions and potential immunogenicity; and administration may cause haemorrhage whilst the prolonged activity of collagenase limits the dose that can be administered locally due to risk of side effects as the drug disperses.

WO 2010/102202 describes a novel temperature sensitive recombinant collagenase in which the activity is observed at significantly below body temperature, but which is comparatively inactive at body temperature. Thus Dupuytren's syndrome can be treated by administering such recombinant collagenase at lower temperatures, which it is claimed restricts the duration of activity, increases the possible local dose and reduces collagenase-related side effects.

To date collagenase therapies have appeared relatively effective in treatment of contracture of the metacarpophalangel joint, whilst the correction of proximal interphalangeal joints has been much less satisfactory. Furthermore, as with surgical interventions, recurrence can be expected, but in the case of early collagenase trials, which involve enzymatically cutting the cord, recurrence is high, especially for disease affecting the proximal interphalangeal joint.

Other non-surgical treatments that have been proposed include application of vitamin E cream applied as topical therapy, ultrasonic therapy and low-dose radiation therapy (for slowing the progression of early stage disease), such as X-rays and electron beam therapy.

Most research for treatments of Dupuytren's disease has focused on detecting pre-disposition to Dupuytren's (e.g. US-A-2004/0161761) and on the extracellular matrices produced, which has resulted in the collagenase-based treatments. There has been very little conclusive insight into potential treatments gained from studies into the biochemical pathway of Dupuytren's disease.

There remains a need for novel therapeutic intervention in the treatment and/or prevention of (e.g. progression of) Dupuytren's disease and other musculoskeletal fibroproliferative disorders.

The present inventors have found that administration of a TNF-α antagonist is surprisingly effective on its own or in combination with another Dupuytren's treatment in preventing the progression of early stage Dupuytren's disease and reversing later stage Dupuytren's disease as well as reducing recurrence of disease.

Problem to be Solved by the Invention

There remains a need for improvements in the treatment of Dupuytren's disease and other musculoskeletal fibroproliferative disorders, particularly fibromatosis and like diseases including and preferably selected from plantar fibromatosis (or Ledderhose's disease), adhesive capsulitis (frozen shoulder) and Peyronie's disease (fibromatosis of the penis).

It is an object of this invention to provide a composition and method for the treatment or prophylaxis (e.g. prevention of progression or recurrence) of one or more of Dupuytren's disease, plantar fibromatosis, adhesive capsulitis and Peyronie's disease.

SUMMARY OF THE INVENTION

In accordance with a first aspect of the invention, there is provided a composition for use in the treatment of a musculoskeletal fibroproliferative disorder, the composition comprising (e.g. a therapeutic, prophylatic or progression-inhibiting effective amount of) a TNF-α antagonist.

In a second aspect of the invention, there is provided a TNF-α antagonist for use in the treatment of a musculoskeletal fibroproliferative disorder. There is also provided the use of a TNF-α antagonist in the manufacture of a medicament for the treatment of a musculoskeletal fibroproliferative disorder.

In a third aspect of the invention, there is provided a composition for use in the treatment of a musculoskeletal fibroproliferative disorder, the composition comprising (e.g. a therapeutic, prophylactic or progression-inhibiting effective amount of) a DAMP antagonist and/or an AGE inhibitor.

In a fourth aspect of the invention, there is provided use of a DAMP antagonist and/or an AGE inhibitor in the manufacture of a medicament for the treatment of a musculoskeletal fibroproliferative disorder.

In a fifth aspect of the invention, there is provided a composition for use in the treatment of a musculoskeletal fibroproliferative disorder, the composition comprising (e.g. a therapeutic, prophylactic or progression-inhibiting effective amount of) a DAMP and/or AGE inflammatory pathway inhibitor.

In a sixth aspect of the invention, there is provided use of a DAMP and/or AGE inflammatory pathway inhibitor in the manufacture of a medicament for the treatment of a musculoskeletal fibroproliferative disorder.

In a seventh aspect of the invention, there is provided a method for the treatment of a musculoskeletal fibroproliferative disorder, the method comprising administering to a patient in need thereof an effective amount of one or more of a DAMP antagonist, an AGE inhibitor or a DAMP and/or AGE inflammatory pathway inhibitor, alone or in combination with an extracellular matrix degradation, depletion or cleavage agent.

In an eighth aspect of the invention, there is provided a method for the treatment of a musculoskeletal fibroproliferative disorder, the method comprising administering to a patient in need thereof an effective amount of a myofibroblast activity down-regulating agent and/or a myofibroblast production inhibitor, such as a TNF-α antagonist, alone or in combination with an extracellular matrix degradation, depletion or cleavage agent.

In a ninth aspect of the invention, there is provided a method for reduction or prevention of recurrence of Dupuytren's disease post-surgical fasciectomy, post-needle fasciotomy or post-enzyme-mediated extracellular matrix degradation, the method comprising locally administering to a patient a myofibroblast activity down-regulating agent and/or a myofibroblast production inhibitor.

Advantages of the Invention

The compositions and methods of the present invention enable progression of Dupuytren's (and other fibromatosis and like disease) to be slowed or halted. It has particular advantages in that early disease state Dupuytren's (and other fibromatosis and like disease) can be prevented from progressing to an established state disease and avoid surgical intervention and the associated recovery time.

Compositions and methods of the present invention enable the treatment, prevention and inhibition of progression of musculoskeletal adhesions such as adhesive capsulitis and tendon adhesion (such as adhesion of the proximal interphalangeal joint in established disease state Dupuytren's disease).

BRIEF DESCRIPTION OF THE DRAWINGS

FIGS. 1A and 1B shows images of nodules and cord in an intraoperative view;

FIGS. 2A and 2B are charts showing a distribution of α-SMA rich cells in tissue excised from different parts of diseased Dupuytren's tissue;

FIGS. 3A, 3B, 3C, 3D and 3E are photographs of a Culture Force Monitor used in in vitro experiments to assess contractile behaviour of cells in a three-dimensional collagen matrix;

FIGS. 4A, 4B and 4C shows graphs of contraction versus time for different cell cultures (in a Culture Force Monitor of FIG. 3) over a 24 hour period;

FIGS. 6A, 6B, 6C and 6D chart mean rate of contraction for cells from different tissue from Dupuytren's patients, the amount of messenger RNA, amount and intracellular distribution of the contractile protein α-smooth muscle actin (α-SMA); FIG. 6E shows images of contractile tissue;

FIGS. 8A, 8B, 8C and 8D show images of sections of Dupuytren's cord samples stained for α-SMA and RAGE;

FIGS. 9A, 9B, 9C and 9D show images of sections of skin samples from Dupuytren's patients stained for RAGE and showing differential distribution in non-palmar and palmar skin;

DETAILED DESCRIPTION OF THE INVENTION

Figure 5:
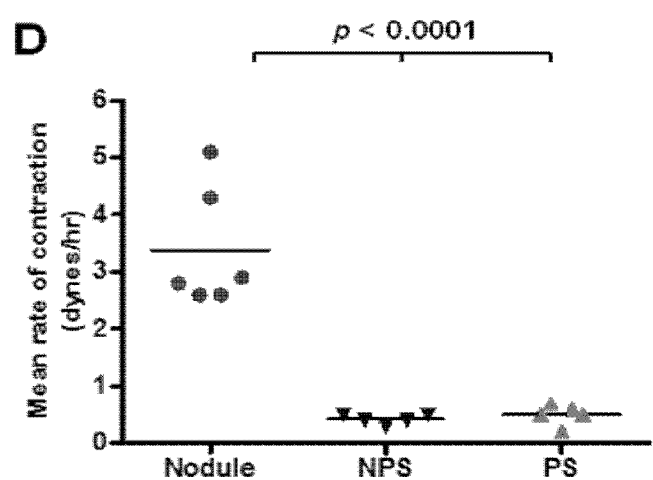
FIG. 5 is a chart showing the mean rate of contraction for cells of different tissue derivation from Dupuytren's patients.

The invention provides for an improved treatment of a musculoskeletal fibroproliferative disorder, especially Dupuytren's disease (or other fibromatosis and like disease such as plantar fibromatosis, adhesive capsulitis and Peyronie's disease), which comprises administration to a patient in need thereof, especially a patient showing signs of early disease state, a therapeutic, prophylactic or progression-inhibitive amount of a myofibroblast activity down-regulating agent and/or a myofibroblast production inhibitor and preferably comprises administration to the patient a therapeutic, prophylactic or progression-inhibitive amount of a TNF-α antagonist. Further, the invention provides, by administration of a TNF-α antagonist to a patient having or showing signs of developing Dupuytren's disease, prevention of disease manifestation and/or progression, optionally as an adjunctive (or concomitant) therapy to a primary surgical intervention (e.g. a fasciotomy or fasciectomy) or primary therapeutic treatment (e.g. an extracellular matrix degradation, depletion or cleaving agent, such as a matrix metalloproteinase or collagenase). Still further, the invention provides, by administration of a TNF-α antagonist to a patient, prevention of recurrence of disease as an adjunctive therapy to primary surgical intervention or therapeutic treatment of established disease.

Musculoskeletal fibroproliferative disorders are characterized by excessive or uncontrolled production of extracellular matrix in association with a musculoskeletal structure, often associated with contraction in later stage disease. As mentioned above, musculoskeletal fibroproliferative disorders include fibromatosis disorders. (The terms 'musculoskeletal fibroproliferative disorders' and 'fibromatosis disease' may be used interchangeably herein, where the context allows). The present invention is concerned with the treatment and, in particular, the inhibition of progression and recurrence (e.g. after primary treatment by surgery or therapy) of such diseases. In particular, the present invention is concerned with diseases selected from Dupuytren's disease, plantar fibromatosis, adhesive capsulitis and Peyronie's disease, especially Dupuytren's disease. The remainder of this document will discuss compositions and methods for treatment of musculoskeletal fibroproliferative disorders generally, with specific reference to Dupuytren's disease.

Where the context allows, it should be understood that the disclosure may be read also with the generality or other specified diseases in place of Dupuytren's disease.

It is believed that the effectiveness of TNF-α antagonists in the treatments of the present invention is due to the dependence on TNF-α of differentiation of fibroblasts into myofibroblasts, which are understood to be the main culprits in contractile activity and induction of uncontrolled extracellular matrix generation in Dupuytren's disease (and other fibromatosis diseases). The inventors have demonstrated this TNF-α dependence and has identified antagonists of TNF-α as viable therapeutics (contrary to the teaching of Goldberg et al, *J Invest Dermatol.* 2007 November; 127(11): 2645-2655, which showed TNF-α suppression of myofibroblast differentiation).

The clinical consensus is currently that clinical nodules are the precursor to established Dupuytren's disease. Dupuytren's disease occurs in people with genetic predisposition and further risk factors to manifestation of Dupuytren's disease include local trauma, poor lifestyle (e.g. smoking and drinking alcohol and poor diet), liver disease and diabetes. Established disease presents as flexion contracture which may typically be presented as contracture of the metacarbophalangeal joints (MCPJ) alone, less frequently contracture of the proximal interphalangeal joints (PIPJ) alone, and often both. A phase III clinical trial of enzymatic fasciotomy using bacterial collagenase reported (Hurst et al, *N. Engl Med,* 2009, 361, 968-979) that 77% of MCPJ contractures were effectively treated (to within 5° of full extension) compared with 40% of PIPJ contractures. An earlier stage trial (Badalamente et al, *J Hand Surg Am,* 2007, 32, 767-774) showed recurrence rates of 57% in patients with PIPJ contractures at 2 years follow-up.

Numerous studies have shown that the presence of myofibroblasts is concomitant with early and active disease and that such cells are implicated in proliferative extra-cellular matrix (ECM) generation or deposition and, in particular, collagen deposition. TGF-β1 leads to the development of the myofibroblast phenotype. Myofibroblasts are also believed to be responsible for contractile behavior. Myofibroblasts characteristically express α-smooth muscle actin (α-SMA), which is the actin isoform typical of vascular smooth muscle cells. α-SMA is believed to be the protein responsible for the contractility of myofibroblasts and is the most reliable marker for myofibroblasts.

As mentioned above, the present invention preferably comprises a composition and method for treating, and more preferably inhibiting or halting the progression or recurrence of, musculoskeletal fibroproliferative disorders, such as fibromatosis disease, especially Dupuytren's disease, by administering to a patient a therapeutic, prophylactic or progression-inhibiting amount of a TNF-α antagonist. Preferably, the administration is local administration (e.g. by injection into or adjacent to the affected tissue).

There are two main embodiments of this invention.

A first main embodiment of the invention comprises a composition and method for treating early disease state musculoskeletal fibroproliferative disorders, especially early disease state Dupuytren's disease, by administering to a patient presenting early state disease, e.g. prior to the presence of palpable cord, an effective amount of a TNF-α antagonist.

According to the first embodiment, a composition comprising a TNF-α antagonist may be administered to a patient for preventing disease progression (to established disease state) and resultant flexion contracture. Preferably, the method comprise local administration (e.g. by injection)

directly into the clinical nodule(s). In a preferred embodiment, the method further comprises administering to the patient, preferably locally (and more preferably directly to the clinical nodule(s) identified), an extracellular matrix degradation, depletion or cleavage agent, which is preferably a collagen degradation, depletion or cleavage agent and may be, for example a matrix metalloproteinase (MMP) and/or a collagenase (but may be, for example, a MMP or collagenase up-regulating or inducing agent). It is believed that the matrix metalloproteinase or collagenase may disrupt collagen and extra-cellular matrix local to the clinical nodule(s) thereby enhancing access of administered TNF-α antagonist to the proliferative fibrotic foci and thus enhance efficacy of treatment. It is believed that administration of the TNF-α antagonist in this manner may be considered prophylactic or progression halting or inhibiting treatment. According to this embodiment, the primary treatment is the TNF-α antagonist to which the extracellular matrix degradation or cleavage agent is preferably adjunctive.

In a preferred embodiment which involves the combined treatment of a patient presenting early disease state musculoskeletal fibroproliferative disorders, especially Dupuytren's disease, with a TNF-α antagonist and an extracellular matrix degradation, depletion or cleavage agent (e.g. matrix metalloproteinase and/or collagenase), the TNF-α antagonist and the extracellular matrix degradation, depletion or cleavage agent (e.g. collagenase) may be administered simultaneously or sequentially, together or separately. Preferably, both TNF-α antagonist and the extracellular matrix degradation, depletion or cleavage agent (e.g. collagenase) are administered locally, for example by injection. Optionally, they may be administered simultaneously, e.g. administering a composition comprising both TNF-α antagonist and collagenase (e.g. by injectable solution) or by applying two separate compositions at the same time. Alternatively, the TNF-α antagonist and the extracellular matrix degradation, depletion or cleavage agent (e.g. collagenase) are administered separately. When administered separately, they may be administered in any order a suitable time apart. Preferably, when administered separately the extracellular matrix degradation, depletion or cleavage agent (e.g. collagenase) is administered first followed by the TNF-α antagonist, which may be administered a suitable time after the TNF-α antagonist, e.g. after no less than 5 minutes, and preferably within 48 hours, more preferably within 24 hours, still more preferably within 6 hours and most preferably within 15 minutes to 3 hours.

Preferably, the TNF-α antagonist and the extracellular matrix degradation, depletion or cleavage agent are administered simultaneously for the treatment of early disease state musculoskeletal fibroproliferative disorders. Preferably, a composition is provided for local administration (e.g. injectable solution, sustained release composition or implant) for treating early disease state musculoskeletal fibroproliferative disorders, preferably Dupuytren's disease, which composition comprises an effective amount of a TNF-α antagonist (or configured to release an effective amount of TNF-α antagonist if, for example, the composition is a sustained release composition) optionally in combination with an extracellular matrix degradation, depletion or cleavage agent (preferably a matrix metalloproteinase and/or collagenase) preferably in an adjunctive amount and a pharmaceutically acceptable carrier.

Preferably, according to this embodiment, the TNF-α antagonist is provided in an amount effective to inhibit disease progression without inducing systemic complications. Optionally, therefore, the TNF-α antagonist is provided in an amount to reduce myofibroblast activity in clinical nodule tissue by at least 10%, preferably at least 30%, more preferably at least 50%, still more preferably at least 75% and most preferably at least 90%, as indicated, for example by, an average α-SMA-positive myofibroblast cell population in clinical nodule tissue by at least 10%, preferably at least 30%, more preferably at least 50%, still more preferably at least 75% and most preferably at least 90%, which activity reduction or cell population reduction is preferably observable within 48 h, more preferably 24 h, from administration. Preferably, an effective amount of TNF-α antagonist is that which will result in a reduction in clinical nodule size (e.g. at least a 20%, or even at least a 50%, reduction in size, as measured by degree of protrusion or lateral or longitudinal extent) in up to two weeks post administration. Efficacy of TNF-α antagonist treatment preferably is observable by an overall reduction in the progression of disease.

Preferably the TNF-α antagonist may be administered in an amount that is in the range 0.01 to 0.5 of the dose indicated (or would be indicated) for systemic treatment of Rheumatoid Arthritis (e.g. by reference to Marketing Authorisation or FDA approval), preferably 0.05 to 0.2 and more preferably 0.095 to 0.15 of the dose. Preferably, the TNF-α antagonist is selected from one or a combination of Infliximab, Adalimumab, Certolizumab pegol, Golimumab or Etanercept and most preferably the TNF-α antagonist is Certolizumab pegol, which is preferably administered in an amount from 1 to 100 mg, preferably 5 to 50 mg and most preferably 10 to 40 mg, e.g. as an injection into the clinical nodule(s). Where more than one injection is provided (e.g. to two distinct clinical nodules), the dose is preferably divided so the total dose provided is in the above range.

Preferably, according to this embodiment, an extracellular matrix degradation, depletion or cleavage agent, e.g. a matrix metalloproteinase and/or collagenase, is provided in a TNF-α antagonist adjunctive amount, by which it is meant an amount effective to enhance the efficacy of the TNF-α antagonist. In any case, it is preferred that the extracellular matrix degradation, depletion or cleavage agent (e.g. matrix metalloproteinase or collagenase) is provided in an amount of up to 1 mg. Preferably, the extracellular matrix degradation, depletion or cleavage agent (e.g. matrix metalloproteinase or collagenase) is administered in an amount significantly below (e.g. 0.01 to 0.5 times) the extracellular matrix degradation, depletion or cleavage agent (e.g. matrix metalloproteinase or collagenase) dose that would be required to achieve an enzymatic fasciotomy in established disease state fibromatosis. Preferably, the extracellular matrix degradation, depletion or cleavage agent (e.g. matrix metalloproteinase or collagenase) is provided in an amount of 0.01 to 0.5 mg, more preferably 0.05 to 0.2 mg.

The extracellular matrix degradation, depletion or cleavage agent, e.g. matrix metalloproteinase or collagenase, may assist the TNF-α antagonist in accessing the cell mass, as well as assisting in disaggregating of the extracellular matrix of the clinical nodule.

A second main embodiment of the invention comprises a composition and method for treating established disease state Dupuytren's (or other musculoskeletal fibroproliferative) disease by administering to a patient an effective amount of a TNF-α antagonist, preferably in combination with, simultaneous to, sequentially with, in association with, concomitantly with, in combined administration with or adjunctive to surgical fasciectomy, a fasciotomy and/or a extracellular matrix degradation, depletion or cleavage agent (e.g. a matrix metalloproteinase or collagenase) treatment, preferably a collagenase treatment. Preferably, the method comprises surgical fasciectomy, needle fasciotomy or extracellular matrix degradation, depletion or cleavage agent (e.g. a matrix metalloproteinase or a collagenase) administration, which provides improvement (i.e. enabling greater extension of the affected digits), more preferably correction (i.e. to within 5° of full extension) and most preferably full correction (complete extension) of the established disease. Most preferably, the method comprises administration of extracellular matrix degradation, depletion or cleavage agent (e.g. a matrix metalloproteinase or a collagenase) to sites local to the disease site. Where the treatment comprises extracellular matrix degradation, depletion or cleavage agent (e.g. a matrix metalloproteinase or a collagenase), the TNF-α antagonist may be provided for combined treatment by simultaneous, sequential or separate administration, e.g. for combined, concomitant or adjunctive therapy. Preferably, in this embodiment, the TNF-α antagonist is adjunctive to the extracellular matrix degradation, depletion or cleavage agent (e.g. a matrix metalloproteinase or a collagenase) treatment. According to this embodiment, the TNF-α antagonist may be administered separately, before or after, administration of the extracellular matrix degradation, depletion or cleavage agent (e.g. a matrix metalloproteinase or a collagenase), e.g. up to 4 to 6 weeks before or after administration of the extracellular matrix degradation, depletion or cleavage agent (e.g. a matrix metalloproteinase or a collagenase), preferably up to 14 days before or after administration of the extracellular matrix degradation, depletion or cleavage agent (e.g. a matrix metalloproteinase or a collagenase), still more preferably at least 30 minutes before or after administration of the extracellular matrix degradation, depletion or cleavage agent (e.g. a matrix metalloproteinase or a collagenase) and more preferably after the extracellular matrix degradation, depletion or cleavage agent (e.g. a matrix metalloproteinase or a collagenase), e.g. in the period 4 hours to 7 days after the extracellular matrix degradation, depletion or cleavage agent (e.g. a matrix metalloproteinase or a collagenase), whereby administration of TNF-α antagonist may gain better access to the disease site but be administered at a point when myofibroblasts can be optimally inhibited.

Preferably, according to this embodiment, the TNF-α antagonist is provided in an amount effective to inhibit disease recurrence without inducing systemic complications. Optionally, therefore, the TNF-α antagonist is provided in an amount to reduce myofibroblast activity in cord tissue or clinical nodules by at least 10%, preferably at least 30%, more preferably at least 50%, still more preferably at least 75% and most preferably at least 90%, compared with post-surgery or fasciotomy (needle or enzyme), as indicated, for example by, an average α-SMA-positive myofibroblast cell population in cord tissue or clinical nodules tissue by at least 10%, preferably at least 30%, more preferably at least 50%, still more preferably at least 75% and most preferably at least 90%, which activity reduction or cell population reduction is preferably observable within 48 h, more preferably 24 h, from administration. Preferably, the recurrence inhibitory effect may be achieved by maintaining populations of α-SMA-positive myofibroblast cells in cord, histological nodule or clinical nodules below 50% of total cell population, preferably below 30% and most preferably below 15%, within, for example, two weeks of administration.

Preferably, an effective amount of TNF-α antagonist is that which will prevent a palpable or as measured (e.g. by ultrasound scan) increase in clinical nodule presentation and/or in clinical nodule size (e.g. a 25% increase in size, as measured by degree of protrusion or lateral or longitudinal extent) in up to two to four weeks post administration. Efficacy of TNF-α antagonist treatment preferably is observable by an overall prevention in the recurrence of disease (e.g. established state disease). Preferably, by administering an effective amount of TNF-α antagonist, re-establishment of established state disease manifested by flexion contracture can be managed or prevented, e.g. flexion contracture maintained to 10° or less, more preferably 5° or less further contraction compared with post-correction treatment extent, within a period after administration of the TNF-α antagonist, e.g. up to 6 weeks, preferably up to 6 months. Optionally, repeat administrations may be provided in order to achieve this (e.g. two to four weekly).

Preferably the TNF-α antagonist may be administered in an amount that is in the range 0.01 to 0.5 of the dose indicated (or would be indicated) for systemic treatment of Rheumatoid Arthritis (e.g. by reference to Marketing Authorisation or FDA approval), preferably 0.05 to 0.2 and more preferably 0.095 to 0.15 of the dose. Preferably, the TNF-α antagonist is selected from one or a combination of Infliximab, Adalimumab, Certolizumab pegol, Golimumab or Etanercept and most preferably the TNF-α antagonist is Certolizumab pegol, which TNF-α antagonist (e.g. Certolizumab pegol) is preferably administered in an amount from 0.1 to 100 mg (e.g. 0.1 or 0.5 to 10 or 20 mg), preferably 1 to 100 mg, more preferably 5 to 50 mg and most preferably 10 to 40 mg, e.g. as an injection into the clinical nodule(s). Where more than one injection is provided (e.g. to two distant or distinct clinical nodules), the dose is preferably divided so the total dose provided is in the above range. Further, it should be noted that the optimal dose may vary according to the TNF-α antagonist used. The optimal dose is preferably a dose which provides the maximum inhibitive effect (on myofibroblast activity and production) for which the isotype antibody at the same dose has no, minimal or acceptably small effect.

Preferably, according to this main embodiment of the invention, the treatment comprises administration local to disease site of an extracellular matrix degradation, depletion or cleavage agent (e.g. a matrix metalloproteinase or a collagenase). The extracellular matrix degradation, depletion or cleavage agent (e.g. a matrix metalloproteinase or a collagenase) should be administered in an amount sufficient to enable improvement and/or correction of disease-associated contraction (e.g. to 5° or less of full extent in the case of Dupuytren's) within 24 or 48 hours of administration). Preferably, an extracellular matrix degradation, depletion or cleavage agent, such as a collagenase (e.g. *Clostridium* collagenase), is provided for local administration in an amount of up to 10 mg administered in one or more locations along each contracture, preferably from 0.1 to 5 mg per administration and more preferably from 0.15 to 2 mg and most preferably 0.5 to 1 mg.

In one embodiment in which extracellular matrix degradation, depletion or cleavage agent (e.g. a matrix metalloproteinase or a collagenase) is administered for contracture improvement and TNF-α antagonist administered for recurrence inhibition, there may be provided a single combined dose of the extracellular matrix degradation, depletion or cleavage agent (e.g. a matrix metalloproteinase or a collagenase) and TNF-α antagonist.

In one embodiment, an extracellular matrix degradation, depletion or cleavage agent may be administered (e.g. injected) into diseased cord tissue in an effective amount, whilst TNF-α antagonist may be administered (e.g. injected) into clinical nodule(s) and/or cord tissue in a recurrence-inhibitory amount.

Any known TNF-α antagonist may be utilized in the implementation of the invention, a broad variety of which are known and disclosed in the art. The TNF-α antagonist is preferably a human TNF-α antagonist. Optionally, the TNF-α antagonist may be an antibody, such as a monoclonal antibody or fragment thereof; a chimeric monoclonal antibody (such as a human-murine chimeric monoclonal antibody); a fully human monoclonal antibody; a recombinant human monoclonal antibody; a humanized antibody fragment; a soluble TNF-α antagonist, including small molecule TNF-α blocking agents such as thalidomide or analogues thereof or PDE-IV inhibitors; a TNF receptor or a TNF receptor fusion protein, e.g. a soluble p55 or p75 TNF receptor or TNF receptor fusion protein.

Optionally, the TNF-α antagonist is a functional fragment or fusion protein comprising a functional fragment of a monoclonal antibody, e.g. of the types mentioned above, such as a Fab, F(ab')$_2$, Fv and preferably Fab. Preferably a fragment is pegylated or encapsulated (e.g. for stability and/or sustained release).

Optionally, the TNF-α antagonist is provided as a bi-functional (or bi-specific) antibody or bi-functional (or bi-specific) antibody fragment. The bi-functional TNF-α antagonist antibody or fragment thereof may be, for example, an antibody, such as a monoclonal antibody or fragment thereof, a chimeric monoclonal antibody (such as a human-murine chimeric monoclonal antibody), a fully human monoclonal antibody, a recombinant human monoclonal antibody, a humanized antibody fragment. Where the TNF-α antagonist comprises a bi-functional antibody fragment or portion, it is preferably a bi-functional F(ab')$_2$ fragment or divalent ScFv, e.g. a bi-specific tandem di-ScFv. In any case, the bi-functional (or bi-specific) antibody or fragment thereof may comprise as one variable domain (e.g. antigen binding portion) a TNF-α antagonist (e.g. a TNF-α antagonist portion of Infliximab, Adalimumab, Certolizumab, Golimumab or Etanercept) and as the other variable domain (e.g. antigen binding portion) a second variable domain other than TNF-α antagonist. Optionally, the second variable domain may comprise an antibody mobility inhibitor, which may be, for example an extracellular matrix, e.g. collagen, binder or antagonist. Thereby, a higher dose of TNF-α antagonist may be administered since the antibody or fragment thereof will be self-localising, minimizing systemic uptake and thus systemic side effects. Optionally, the second variable domain may comprise a DAMP antagonist (such as an antagonist for S100A8 and/or S100A9, e.g. as described in U.S. Pat. No. 7,553,488) or an AGE inhibitor (e.g. being variable domains of DAMP antagonist antibody or AGE inhibitor antibody). Methods for the production of bi-functional antibodies, and bi-functional antibody fragments are known in the art, which methods may be applied to the present purpose.

Preferably, the TNF-α antagonist is selected from those which at administration (e.g. local administration, such as injection into clinical nodule or cord) cause administration-site irritation manifested as palpable local swelling, redness and pruritis in fewer than 40% of patients, preferably fewer than 20% and more preferably fewer than 10%.

The TNF-α antagonist may be selected, for example, from one or a combination of Infliximab, Adalimumab, Certolizumab pegol, Golimumab or Etanercept, or functional fragment thereof. Most preferably, the TNF-α antagonist is Certolizumab pegol, since it causes low injection site reaction and pain.

It is particularly advantageous according to the present invention to minimize inflammation, irritation and pain associated with administration since local irritation may limit patient acceptability and furthermore local inflammation may lead to recurrence of disease. In one embodiment, the TNF-α antagonist may be administered with or prior to an extracellular matrix (ECM) degradation or cleavage agent (e.g. collagenase) whereby the inflammatory response to ECM degradation may be minimised, thereby reducing the likelihood of treatment induced recurrence.

The extracellular matrix (ECM) degradation, depletion or cleavage agent may be any suitable agent capable of degrading, cleaving or causing or inducing degradation or cleavage of extracellular matrix, including fibronectin and collagen. For example, the ECM degradation or cleavage agent may be an ECM degradation enzyme or an ECM degradation enzyme expression up-regulator (e.g. relaxin). Preferably the ECM degradation or cleavage agent is a matrix metalloproteinase or a collagenase, more preferably a collagenase, such as a bacterial collagenase (e.g. clostridial collagenase), human or humanised collagenase or mutant or recombinant collagenase or recombinant matrix metalloproteinase (e.g. recombinant matrix metalloproteinase I, preferably human recombinant matrix metalloproteinase I). Preferably, the collagenase is time or temperature dependent or is photodynamically activated or deactivated, to allow higher local doses to be administered without systemic or long-lasting side-effects. Optionally, it is a Cathespin-L or a mutant or recombinant thereof. Examples of suitable collagenase for use in the present invention include those described in: GB-A-2323530, U.S. Pat. No. 5,589,171, USRE39941, U.S. Pat. No. 6,086,272 & WO-A-2010/102262 (and for established disease optionally in the amounts described therein, the disclosure of which collagenases and amounts and modes of administration are incorporated herein by reference).

By early disease state it is meant that indications of disease are present, e.g. histological markers or more particularly clinical nodules in tissue, but in the absence of, for example, palpable cord or significant contracture. By early disease state Dupuytren's disease, it is meant that indications of Dupuytren's disease are present, e.g. histological markers or more particularly clinical nodules in palmar and/or digital tissue, but in the absence of significant (e.g. at least 5°) flexion contracture (or, for example, palpable cord).

By established disease state, it is meant that clinical nodules are present, palpable cord is present and contracture is evident. By established disease state Dupuytren's disease, it is meant that clinical nodules are present on the palm and digits of the hand and flexion contracture is evident (e.g. at least 5°).

Varying histological stages of Dupuytren's disease have been categorised in the literature, most succinctly by Rombouts (J Hand Surg Am, 14, 644-652, 1989) and later authors, into three distinct stages: 1) a proliferative stage with high cellularity and the presence of mitotic figures; 2) a fibrocellular stage charactised by high cellularity but no mitotic figures and the presence of reticulin network; and 3) a fibrous stage with few cells separated by broad bundles of collagen fibres. Stage 1) disease is believed to correlate with early disease state as discussed above (i.e. presence of nodules but no contracture) and Dupuytren's stages 2) and 3) is believed to correlate with our Established Disease State (characterized by digital contracture). The present inventors have found that during early established disease state, active myofibroblasts are collected in the established nodules and cords, especially in relation to the MCP and PIP joints and these drive the progression of flexion contractures of the digit.

By clinical nodule, it is meant a palmar or digital nodule evident as a palpable subcutaneous lump.

By histological (or histopathological) nodule, it is meant a collection of cells (mainly myofibroblast cells with some inflammatory cells such as macrophages and mast cells) typically in a whorled pattern and which may range from tiny foci of cells to larger collections of cells, but not clinically palpable.

Without being bound by theory, it is believed that the initial clinically palpable nodule(s) is the focus of proliferating fibroblasts in disease progression, but that numerous histological nodules will form at various locations in the palm and/or digits which will ultimately contribute to cord formation, contraction and flexion contracture.

Where 'nodule' is used herein it may be clinical or histological nodules (or either) as will be apparent from the context.

According to two alternative embodiments specific to Dupuytren's, a first embodiment may relate to a composition and method for treating Dupuytren's disease characterized by joint contractures of less than 20° and a second embodiment may relate to a composition and method for treating Dupuytren's disease characterized by joint contractures of at least 20°. The contracture of 20° is identified as a transition phase, since at less than 20° contracture, many patients may choose to stop progression of the disease without wishing to undergo surgery since their mobility and operative use of the hand is still largely adequate, whilst at greater than 20°, many patients will find surgery or other collagen depleting therapy (such enzymatic fasciotomy) essential to restore full function to the hand.

The inventors' investigations reveal that TNF-α as an optimal therapeutic target for early Dupuyten's disease (i.e. early disease state). In established disease state Dupuytren's disease, an ideal combination is a matrix metalloproteinase such as collagenase with a TNF-α antagonist to inhibit recurrence, which is typically associated with enzymatic fasciotomy.

As mentioned above, myofibroblasts are implicated in two ways in the development of musceloskeletal fibroproliferative disorders and, in particular, Dupuytren's disease. They are responsible for extracellular matrix production or deposition and contractile behavior. It is believed that the activity of myofibroblasts is mediated by α-SMA, which is over-expressed in active myofibroblast cells. Without being bound by theory, the present inventors have found that TNF-α is implicated in the activity of myofibroblasts in Dupuytren's disease in at least two ways—firstly, by reducing the activity of myofibroblast; and secondly by enhancing the production or attraction of myofibroblasts.

In each of the embodiments, the TNF-α antagonist may be provided in a multiple administrations over an extended (or continuous) term in order to prevent or inhibit disease progression or recurrence. Where recurrence is to be avoided, intermittent treatment may be provided by, e.g. low-dose fortnightly, monthly or six-monthly administration. Alternatively, continuous treatment may be provided by low-dose releasing sustained or delayed intermittent release implant or patch. Alternatively, repeat doses may be initiated by signs of disease progression in the early disease state and may optionally comprise a combined extracellular matrix degradation or cleavage agent (e.g. a matrix metalloproteinase or a collagenase) and TNF-α antagonist treatment (e.g. consistent with the first embodiment described above).

In one embodiment of the invention, the progression of early disease state disease (e.g. Dupuytren's disease) to established disease state can be prevented, inhibited or halted by the local administration of a TNF-α antagonist.

Preferably, the TNF-α antagonist may be administered separately or simultaneously in combination with or adjunctively to a collagenase and/or matrix metalloproteinase. A collagenase, especially a photo-responsive or temperature dependent collagenase, may be administered for local effect to enhance the TNF-α antagonist disease progression inhibition effect by enhancing access to treatment sites by cleaving early stage extracellular matrix formation. A temperature dependent collagenase is one which (typically a recombinant or mutant collagenase) has collagenase activity dependent upon temperature and typically is active at below body temperature, e.g. at 25° C. and below, thereby allowing extremely high doses of collagenase to act very locally (e.g. by injecting at the disease site at say 20° C. without having any systemic action or other side effects associated with longevity of action). TNF-α antagonist have a further beneficial effect since it will reduce inflammation at the nodule site and thus reduce development and recruitment of further myofibroblasts.

The composition and method of the present invention may utilise any suitable means of administration, which is preferably local. In particular, the TNF-α antagonist should be administered locally, e.g. by applying directly into a surgical incision during surgery, by injection (preferably directly into the clinical nodule(s) and/or cord tissue), by release from a sustained and/or delayed release lozenge or device that may be implanted into or close to the disease site or a sustained and/or delayed release patch formulation, by topical application or any other suitable route. A composition is preferably suitably formulated and typically comprises the required dose of TNF-α antagonist along with a pharmaceutical acceptable carrier or excipient.

Formulations for parenteral administration may typically comprise a sterile aqueous preparation of the active ingredient, which is preferably isotonic with the blood of the recipient. Formulations for intra-articular administration may be in the form of a sterile aqueous preparation of the active ingredient. Formulations suitable for topical administration may include liquid and semi liquid preparations such as liniments, lotions and applications; oil-in-water and water-in-oil emulsions such as creams, ointments and pastes; and solutions and suspensions.

In a further aspect, there is provided a formulation for frequent, e.g. daily, periodic or occasional (preferably daily), topical application to the musculoskeletal fibroproliferative disorder area (e.g. the hands, and in particular palms and digits, in the case of Dupuytren's disease) for use, for example, by early disease state or post-operative patients for the inhibition of disease progression or recurrence, the formulation comprising a TNF-α antagonist suitable for topical administration (e.g. selected from such TNF-α antagonists defined above) and a suitable excipient. The formulation may be provided as a cream or lotion, a patch or a medicated glove (in which the glove is impregnated for release of the active component from the internal surface). Preferably, the formulation comprises TNF-α antagonist in a concentration for administration by topical application of a low dose, such as 0.001 to 0.05, preferably 0.001 to 0.01, of the systemic dose of the TNF-α antagonist. Optionally, the formulation further comprises a DAMP antagonist and/or an AGE inhibitor.

Optionally, the compositions and methods of the present invention may further comprise further active ingredients that may be effective in the treatment or progression-inhibition of musculoskeletal fibroproliferative disorders such as Dupuytren's disease. For example, combination therapy or concomitant or adjunctive co-administration of a TNF-α antagonist and an agent of the vascular endothelial growth factor family, such as VEGF-A, VEGF-B, VEGF-C or VEGF-D or an agent encoding said VEGF or a functional fragment thereof (such as described in WO-A-2004/082705), which combination is preferably a development retarding combination (or composition) for use in association with surgery, or needle or enzyme fasciotomy. Additionally or alternatively such method or composition as described herein may further comprise an activator of PPARγ (such as pioglitazone) for reducing myofibroblast populations local to the disease site (and enhancing the TNF-α antagonist activity).

In the treatment of musculoskeletal fibroproliferative disorders and, preferably, Dupuytren's disease, there is as a further aspect provided a composition for use in such treatment which comprises a matrix metalloproteinase or collagenase (or matrix metalloproteinase or collagenase up-regulator) in combination with a myofibroblast activity down-regulator and/or a myofibroblast production (or differentiation) inhibitor each preferably in appropriate therapeutic amounts according to the respective embodiment as discussed above. The preferred myofibroblast activity down-regulator and/or myofibroblast production (or differentiation) inhibitor is TNF-α antagonist.

In a further aspect there is provided a method for the reduction or prevention of recurrence of musculosekeletal fibroproliferative disorder, especially Dupuytren's disease, which comprises, after surgical, needle fasciotomy or enzyme fasciotomy, administration of a myofibroblast de-activating and/or producing inhibition agent local to the disease site. Preferably the agent is a TNF-α antagonist, preferably administered in the aforementioned doses (relative the second main embodiment).

In a further aspect of the invention, there is provided a method and composition for the treatment of a musculoskeletal fibroproliferative disorder, especially Dupuytren's disease, which comprises a DAMP (damage associated molecular patterns) antagonist. The musculoskeletal fibroproliferative disorder may be a fibromatosis and may preferably be selected from plantar fibromatosis, adhesive capsulitis, Peyronie's disease or Dupuytren's disease and is preferably Dupuytren's disease. The method preferably comprises administering an effective amount of a DAMP antagonist locally to the disease site, e.g. by injection into clinical nodules of early disease state tissue or into nodules and/or cord of established disease state tissue or by application of a sustained release patch or implant or application of a cream (or other such topical formulation). The composition according to this aspect preferably comprises a DAMP antagonist in an effective amount and a pharmaceutically acceptable excipient.

There have been observed some evidence to support a higher incidence of Dupuytren's disease in manual workers and association between injury, surgery and infection and Dupuytren's disease has been observed. Without being bound by theory, it is believed that DAMPs and, in particular, a sub-group of DAMPs, Alarmins released as a result of trauma to the hand (or local area which disease affects) catalyse or induce myofibroblast production and/or myofibroblast activity (including contraction), especially in those genetically predisposed to the disease. It is believed that the Alarmins directly and/or indirectly induce myofibroblast activity and/or production by direct biochemical pathway for differentiation of fibroblasts to active myofibroblasts and indirectly by up-regulating TNF-α production (which itself promotes myofibroblast activity and production direction and through inflammation-induced stress as discussed above). The Alarmins include HMGB-1 (high mobility group box protein), S100 A8, S100 A9, S100 A8/9 and S100 A12 and most implicated is S100 A8. The DAMP antagonist according to the method and composition according to this aspect of the invention is preferably an Alarmin antagonist and more preferably one or more antagonist of one or more of HMGB-1, S100 A8, S100 A9, S100 A8/9 and S100 A12, most preferably an S100 A8 antagonist, e.g. an inactive fragment of S100 A8 to act as S100 A8 receptor blocker. Without being bound by theory, it is believed that S100 A8 (and other alarmins) elicit their inflammatory effect by binding TLR 4 (toll like receptor 4) and thus TLR 4 blockers may be considered S100 A8 antagonists.

Preferably, the DAMP antagonists of this aspect are for use in prevention or inhibition of the onset and/or development of disease in pre-disease and early disease state patients, especially trauma-induced early disease state patients (especially of Dupuytren's disease). Alternatively or additionally, the DAMP antagonists of this aspect are for use in prevention or inhibition of recurrence of disease in post-treatment patients having established state disease (e.g. after surgery or needle or enzyme fasciotomy), e.g. adjunctive to such primary treatment, which is particularly beneficial since the primary treatment is at risk of causing trauma-induced DAMP up-regulation and release and associated myofibroblast activation. Accordingly, the DAMP antagonist is preferably used in an amount effective to prevent or inhibit disease onset, progression or recurrence without inducing systemic complications. Optionally, therefore, the DAMP antagonist is provided in an amount to reduce myofibroblast activity in cord tissue or clinical nodules by at least 5%, preferably at least 10% and more preferably at least 30% and optionally 50% or more, 75% or more or even 90% or more, compared with post-trauma or post-surgery or fasciotomy (needle or enzyme), as indicated, for example by, an average α-SMA-positive myofibroblast cell population in cord tissue or clinical nodules tissue by at least 10%, preferably at least 30%, more preferably at least 50%, still more preferably at least 75% and most preferably at least 90%, which activity reduction or cell population reduction is preferably observable within 48 h, more preferably 24 h, from administration. Preferably, the recurrence inhibitory effect may be achieved by maintaining populations of α-SMA-positive myofibroblast cells in cord, histological nodule or clinical nodules below 50% of total cell population, preferably below 30% and most preferably below 15%, within, for example, two weeks of administration.

Preferably, an effective amount of DAMP antagonist is that which will prevent a palpable increase in clinical nodule presentation and/or in clinical nodule size (e.g. a 25% increase in size, as measured by degree of protrusion or lateral or longitudinal extent) in up to two to four weeks post administration. Efficacy of DAMP antagonist treatment preferably is observable by an overall prevention in the onset or development of disease in post-trauma patients or in overall prevention of recurrence of disease (e.g. established state disease) in post-surgery patients. Preferably, by administering an effective amount of DAMP antagonist (after primary treatment and intermittently in response to local trauma), re-establishment of established state disease manifested by flexion contracture can be managed or prevented, e.g. flexion contracture maintained to 10° or less, more preferably 5° or less further contraction compared with post-correction treatment extent, within a period after administration of the DAMP antagonist, e.g. up to 6 weeks, preferably up to 6 months. Optionally, repeat administrations may be provided in order to achieve this (e.g. two to four weekly or responsive to local trauma).

Optionally, the DAMP antagonist of this aspect of the invention may be co-administered or administered in combination (e.g. simultaneously or sequentially) with a TNF-α antagonist whereby two pathways to myofibroblast activation may be controlled. In one embodiment, there is provided a composition for the treatment of a musculoskeletal fibroproliferative disorder such as Dupuytren's disease, which comprises an effective combined amount of a DAMP antagonist and a TNF-α antagonist and a pharmaceutically acceptable excipient. The composition may be administered by injection (or other application) to the disease site (e.g. clinical nodules or cord tissue) or by application of a patch or by delayed and/or sustained release for local administration (e.g. implant) or topical application.

Optionally, the actives and compositions of this aspect of the invention may be provided as combined, concomitant or adjunctive treatment with an extracellular matrix degradation, depletion or cleavage agent as and in the manner hereinbefore described (e.g. in place of and/or in addition to TNF-α antagonist).

In another aspect of the invention there is provided a method for the modulation of myofibroblast activity by DAMP agonism/antagonism, e.g. by administration of a DAMP agonist or antagonist. There is also provided a composition for up-regulating myofibroblast activity comprising a DAMP agonist and a composition for down-regulation myofibroblast activity comprising a DAMP antagonist. The DAMP agonist or antagonist being provided in a myofibroblast modulating amount, optionally formulated for local administration.

Optionally, the DAMP antagonist is provided as a bi-functional (or bi-specific) antibody or bi-functional (or bi-specific) antibody fragment. The bi-functional DAMP antagonist antibody or fragment thereof may be, for example, an antibody, such as a monoclonal antibody or fragment thereof, a chimeric monoclonal antibody (such as a human-murine chimeric monoclonal antibody), a fully human monoclonal antibody, a recombinant human monoclonal antibody, a humanized antibody fragment. Where the DAMP antagonist comprises a bi-functional antibody fragment or portion, it is preferably a bi-functional $F(ab')_2$ fragment or divalent ScFv, e.g. a bi-specific tandem di-ScFv. In any case, the bi-functional (or bi-specific) antibody or fragment thereof may comprise as one variable domain (e.g. antigen binding portion) a DAMP antagonist (such as an antagonist for S100A8 and/or S100A9, e.g. as described in U.S. Pat. No. 7,553,488) and as the other variable domain (e.g. antigen binding portion) a second variable domain other than DAMP antagonist. Optionally, the second variable domain may comprise an antibody mobility inhibitor, which may be, for example an extracellular matrix, e.g. collagen, binder or antagonist. Thereby, a higher dose of DAMP antagonist may be administered since the antibody or fragment thereof will be self-localising, minimizing systemic uptake and thus systemic side effects. Optionally, the second variable domain may comprise an AGE inhibitor (e.g. being variable domains of DAMP antagonist antibody or AGE inhibitor antibody). Methods for the production of bi-functional antibodies, and bi-functional antibody fragments are known in the art, which methods may be applied to the present purpose.

Optionally, treatment of a patient with DAMP antagonist, optionally in combination with TNF-α antagonist, may be indicated for patients with early disease state (for inhibition of disease progression) or post-surgery (for recurrence inhibition) for patients who disease area (e.g. hands in the case of Dupuytren's is subject to local trauma), such as, in the case of Dupuytren's disease, golfers, builders or drivers etc.

Optionally, e.g. for patient's for whom local trauma is a causative factor in the musculoskeletal fibroproliferative disorder, especially Dupuytren's disease, there is provided (as a further aspect) a formulation for frequent, e.g. daily, periodic or occasional (preferably daily), topical application to the musculoskeletal fibroproliferative disorder area (e.g. the hands, and in particular palms and digits, in the case of Dupuytren's disease) for use, for example, by early disease state or post-operative patients for the inhibition of disease progression or recurrence, the formulation comprising a DAMP antagonist suitable for topical administration (e.g. an S100 A8 and/or A9 antagonist) and a suitable excipient. The formulation may be provided as a cream or lotion, a patch or a medicated glove (in which the glove is impregnated for release of the active component from the internal surface). Preferably, the formulation comprises a DAMP antagonist in a concentration for administration by topical application of a low dose, such as 0.001 to 0.05, preferably 0.001 to 0.01, of the systemic dose of the DAMP antagonist. Optionally, the formulation further comprises an AGE inhibitor.

In a still further aspect of the invention, there is provided a method and composition for the treatment of a musculoskeletal fibroproliferative disorder, especially Dupuytren's disease, which comprises an AGE (advanced glycation end products) inhibitor. The musculoskeletal fibroproliferative disorder may be a fibromatosis and may preferably be selected from plantar fibromatosis, adhesive capsulitis, Peyronie's disease or Dupuytren's disease and is preferably Dupuytren's disease. The method preferably comprises administering an effective amount of an AGE inhibitor locally to the disease site, e.g. by injection into clinical nodules of early disease state tissue or into nodules and/or cord of established disease state tissue or by application of a sustained release patch or implant or application of a cream (or other such topical formulation). The composition according to this aspect preferably comprises an AGE inhibitor in an effective amount and a pharmaceutically acceptable excipient.

There is a statistically significant association of Dupuytren's disease with smoking, alcohol consumption and diabetes mellitus. The present inventors propose that AGE may be implicated in the association and biochemical pathway driving Dupuytren's disease in genetically predisposed patients who smoke, drink or have diabetes. AGE-modified proteins are the final products formed from irreversible non-enzymatic glycation between reducing sugars and polypeptides and have been shown to exert their influence by forming protein cross-links that alter extracellular matrix structure as well as interacting with cell surface receptors. Without being bound by theory, it is believed that AGEs and their receptors RAGE are implicated in the early stages and development of Dupuytren's disease and that AGEs up-regulate myofibroblast activity both direction and indirectly. It is believed that AGEs present in pre-disease or early disease palmar tissue present due to increased levels associated with lifestyle choices or diabetes catalyse or induce myofibroblast production and/or myofibroblast activity (including contraction), especially in those genetically predisposed to the disease. It is believed that the AGEs directly and/or indirectly induce myofibroblast activity and/or production by direct biochemical pathway for differentiation of fibroblasts to active myofibroblasts and indirectly by up-regulating TNF-α production (which itself promotes myofibroblast activity and production direction and through inflammation-induced stress as discussed above).

Preferably, the AGE inhibitors of this aspect are for use in prevention or inhibition of the onset and/or development of disease in pre-disease and early disease state patients (especially of Dupuytren's disease). Alternatively or additionally, the AGE inhibitors of this aspect are for use in prevention or inhibition of recurrence of disease in post-treatment patients having established state disease (e.g. after surgery or needle or enzyme fasciotomy), e.g. adjunctive to such primary treatment. Accordingly, the AGE inhibitor is preferably used in an amount effective to prevent or inhibit disease onset, progression or recurrence without inducing systemic complications. Optionally, therefore, the AGE inhibitor is provided in an amount to reduce myofibroblast activity in cord tissue or clinical nodules by at least 5%, preferably at least 10% and more preferably at least 30% and optionally 50% or more, 75% or more or even 90% or more, compared with post-surgery or fasciotomy (needle or enzyme), as indicated, for example by, an average α-SMA-positive myofibroblast cell population in cord tissue or clinical nodules tissue by at least 10%, preferably at least 30%, more preferably at least 50%, still more preferably at least 75% and most preferably at least 90%, which activity reduction or cell population reduction is preferably observable within 48 h, more preferably 24 h, from administration. Preferably, the recurrence inhibitory effect may be achieved by maintaining populations of α-SMA-positive myofibroblast cells in cord, histological nodule or clinical nodules below 50% of total cell population, preferably below 30% and most preferably below 15%, within, for example, two weeks of administration.

Preferably, an effective amount of AGE inhibitor (e.g. pimagedine) is that which will prevent a palpable increase in clinical nodule presentation and/or in clinical nodule size (e.g. a 25% increase in size, as measured by degree of protrusion or lateral or longitudinal extent) in up to two to four weeks post administration. Efficacy of AGE inhibitor treatment preferably is observable by an overall prevention in the onset or development of disease in post-trauma patients or in overall prevention of recurrence of disease (e.g. established state disease) in post-surgery patients or prevention of progression of early disease. Preferably, by administering an effective amount of AGE inhibitor (after primary treatment), re-establishment of established state disease manifested by flexion contracture can be managed or prevented, e.g. flexion contracture maintained to 10° or less, more preferably 5° or less further contraction compared with post-correction treatment extent, within a period after administration of the AGE inhibitor, e.g. up to 6 weeks, preferably up to 6 months. Optionally, repeat administrations may be provided in order to achieve this (e.g. two to four weekly or responsive to local trauma).

Any suitable AGE inhibitor may be utilized according to this aspect of the invention.

Optionally, the AGE inhibitor of this aspect of the invention may be co-administered or administered in combination (e.g. simultaneously or sequentially) with one or both of a DAMP antagonist and a TNF-α antagonist whereby at least two pathways to myofibroblast activation may be controlled. In one embodiment, there is provided a composition for the treatment of a musculoskeletal fibroproliferative disorder such as Dupuytren's disease, which comprises an effective combined amount of an AGE inhibitor and a DAMP antagonist and/or a TNF-α antagonist and a pharmaceutically acceptable excipient. The composition may be administered by injection (or other application) to the disease site (e.g. clinical nodules or cord tissue) or by application of a patch or by delayed and/or sustained release for local administration (e.g. implant) or topical application.

Optionally, the actives and compositions of this aspect of the invention may be provided as combined, concomitant or adjunctive treatment with an extracellular matrix degradation, depletion or cleavage agent as and in the manner hereinbefore described.

Optionally, the AGE inhibitor is provided as a bi-functional (or bi-specific) antibody or bi-functional (or bi-specific) antibody fragment. The bi-functional AGE inhibitor antibody or fragment thereof may be, for example, an antibody, such as a monoclonal antibody or fragment thereof, a chimeric monoclonal antibody (such as a human-murine chimeric monoclonal antibody), a fully human monoclonal antibody, a recombinant human monoclonal antibody, a humanized antibody fragment. Where the AGE inhibitor comprises a bi-functional antibody fragment or portion, it is preferably a bi-functional $F(ab')_2$ fragment or divalent ScFv, e.g. a bi-specific tandem di-ScFv. In any case, the bi-functional (or bi-specific) antibody or fragment thereof may comprise as one variable domain (e.g. antigen binding portion) an AGE inhibitor and as the other variable domain (e.g. antigen binding portion) a second variable domain other than AGE inhibitor. Optionally, the second variable domain may comprise an antibody mobility inhibitor, which may be, for example an extracellular matrix, e.g. collagen, binder or antagonist. Thereby, a higher dose of AGE inhibitor may be administered since the antibody or fragment thereof will be self-localising, minimizing systemic uptake and thus systemic side effects. Methods for the production of bi-functional antibodies, and bi-functional antibody fragments are known in the art, which methods may be applied to the present purpose.

Optionally, treatment of a patient with an AGE inhibitor, optionally in combination with TNF-α antagonist, may be indicated for patients with early disease state (for inhibition of disease progression) or post-surgery (for recurrence inhibition) for patients who are diabetic or who smoke or drink (greater than the WHO recommended amount).

Optionally, e.g. for patients for whom diabetes or lifestyle (e.g. smoking and/or drinking excessive alcohol) is considered a causative factor in the musculoskeletal fibroproliferative disorder, especially Dupuytren's disease, there is provided (as a further aspect) a formulation for frequent, e.g. daily, periodic or occasional (preferably daily), topical application to the musculoskeletal fibroproliferative disorder area (e.g. the hands, and in particular palms and digits, in the case of Dupuytren's disease) for use, for example, by early disease state or post-operative patients for the inhibition of disease progression or recurrence, the formulation comprising an AGE inhibitor suitable for topical administration and a suitable excipient. The formulation may be provided as a cream or lotion, a patch or a medicated glove (in which the glove is impregnated for release of the active component from the internal surface). Preferably, the formulation comprises an AGE inhibitor in a concentration for administration by topical application of a low dose, such as 0.001 to 0.05, preferably 0.001 to 0.01, of the systemic dose of the AGE inhibitor.

In another aspect of the invention there is provided a method for the modulation of myofibroblast activity by AGE promotion/inhibition, e.g. by administration of an AGE promoter or inhibitor. There is also provided a composition for down-regulation myofibroblast activity comprising a AGE inhibitor.

In each embodiment, repeat administrations may be necessary (e.g. injections). Furthermore, the treatment may need to be repeated to manage or control disease progression or recurrence over a period of months or years if indications of recurrence or onset are detected (or as a matter of course)

In a yet further aspect, there is provided a method and composition for the treatment, prophylaxis or progression-inhibition of musculoskeletal adhesions by administering to a patient in need thereof a therapeutic, prophylactic or progression-inhibiting amount of a myofibroblast activity regulator, e.g. an agent for the de-activation of myofibroblast and/or inhibiting the production of myofibroblast.

Preferably, the composition comprises, as an agent for the de-activation of myofibroblast and/or inhibiting the production of myofibroblast, one or a combination of a TNF-α antagonist, a DAMP antagonist, an AGE inhibitor, or a DAMP and/or AGE inflammatory pathway inhibitor. Preferably, the method and composition comprises a TNF-α antagonist. Optionally, other agents may be used in such treatment including an agent of the vascular endothelial growth factor family, such as VEGF-A, VEGF-B, VEGF-C or VEGF-D or an agent encoding said VEGF or a functional fragment thereof (such as described in WO-A-2004/082705), and/or an activator of PPARγ (such as pioglitazone).

DAMP and/or AGE inflammatory pathway inhibitors as referred to herein include inhibitors or antagonists of any receptors or upstream or downstream signalling components. For example DAMP inflammatory pathway inhibitors may include TLR (toll like receptor) antagonists (e.g. TLR-4 antagonists) or Myd88 antagonists or Myd88 down-regulators, since it is believed that TLR-4 and Myd88 are implicated in the DAMP mediated inflammatory pathway. For example, AGE inflammatory pathway inhibitors may include RAGE inhibitors or antagonists. Optionally, according to a further aspect of the invention, the above aspects and embodiments may be modified by substitution or addition of TNF-α antagonist with DAMP and/or AGE inflammatory pathway inhibitors.

By musculoskeletal adhesions, it is meant a sub-set of musculoskeletal fibroproliferative disorders in which excess fibrotic tissue or scar tissue is formed adjacent or in association with a tendon, muscle, joint, ligament or fascia causing an adhesion. Examples of such musculoskeletal adhesions include periarticular fibrosis (e.g. about the proximal interphalangeal joint) and adhesive capsulitis. Preferably, according to this aspect, there is provided a composition and treatment for a condition selected from perarticular fibrosis (e.g. of the proximal interphalangeal joint), spinal adhesions (e.g. post-surgical) and adhesive capsulitis.

In one particular embodiment, there is a method for the prevention of recurrence of Dupuytren's disease comprising administering (e.g. post-surgery, post-needle fasciotomy or after or in association with enzyme fasciotomy) a TNF-α antagonist to the nodule(s) and/or cord and administering a TNF-α antagonist to the tissue adjacent the proximal interphalangeal joint, whereby simultaneously treatment to prevent recurrence of Dupuytren's disease (and digital contracture) and reduction in formation and persistence of fibrotic scar tissue about the joint can be achieved. It is believed that the effectiveness of, e.g. a collagenase treatment, of Dupuytren's disease (which suffers from a high rate of recurrence especially about the proximal interphalangeal joint) will be enhanced by co-therapy with a TNF-α antagonist (or other agent for the de-activation of myofibroblast and/or inhibiting the production of myofibroblast) by administering the same to clinical nodules and/or cord tissue and to subcutaneous tissue (e.g. fibrotic scar tissue) adjacent the proximal interphalangeal joint.

For adhesive capsulitis (or frozen shoulder), preferably the treatment comprises one or both of a TNF-α antagonist and an AGE inhibitor or DAMP antagonist.

In an alternative embodiment in each of the above mentioned aspects and embodiments, a TNF-α production or activity inhibitor may be used in place of or together with a TNF-α antagonist.

The composition may be formulated for administration to and/or adjacent to the affected tissue (e.g. by injection, deposition during surgery or preferably by topical application) whereby doses in the ranges described above in relation to musculoskeletal fibroproliferative disorders (e.g. Dupuytren's disease) are achieved/provided. Topical formulations and combinations as described above are also included.

The invention will now be described and illustrated in more detail, without limitation, with reference to the following Examples.

EXAMPLES

The following studies were undertaken to understand better the progression of Dupuytren's disease. Tissue was taken from nodules and cords from Dupuytren's patients and compared with non-disease palmar tissue from the same patients. Studies were carried out in a culture force monitor developed to ensure that myofibroblast populations can be monitored in an environment more akin to that present in diseased tissue (in line with that set out in Verjee et al, J Hand Surg Am, 34, 1785-1794 and J Cell Physiol 224, 681-690). Four examples are described below—Example 1 is concerned with presence, distribution and behavior of myofibroblast cells in diseased tissue; Example 2 is concerned with the role of inflammation in Dupuytren's disease; Example 3 examines advanced glycation end products in Dupuytren's; and Example 4 examines the role of DAMPs in Dupuytren's.

Example 1

Over 100 Dupuytren's patient samples were collected to examine myofibroblast distribution. Our data on >100 Dupuytren's cords show that in the majority of patients, myofibroblasts are concentrated in nodules, located in the palm and at the level of the affected joints (see FIG. 1). According to FIGS. 1A and 1B, nodules rich in myofibroblasts are located in the vicinity of the finger joints. FIG. 1A shows: intraoperative view of Dupuytren's cord, with location of proximal interphalangeal joint (PIPJ; 1) marked; FIG. 1B shows: Low magnification photomicrograph of histological section stained for α-smooth muscle actin. A collection of α-SMA rich cells in a nodule is located in the vicinity of the PIPJ; and High magnification view of nodular area, showing α-SMA positive cells (myofibroblasts).

Of over 100 cords analysed, more than 60% contained nodules. Although there was marked heterogeneity, nodules were very cellular, with approximately 2.5 thousand cells per $mm^2$ arranged in whorls. On average, 99% of the cells were α-SMA positive. In peri-nodular areas, there were fewer cells, approximately 800 per mm² and, on average, one third were α-SMA positive.

FIGS. 2A and 2B shows that nodules are mostly cellular and are rich in α-SMA positive cells. Examination of 24 Dupuytren's patient samples by electron microscopy showed that clinical recurrence was not related to patient age at onset, duration, or severity of disease. Histological nodules were seen as frequently in samples from both primary and recurrent disease (two-thirds of cords in each case) and there was also no significant difference in digital contracture between primary and recurrent disease. Furthermore, there was also no difference in nodular surface area between primary dermofasciectomy samples, primary fasciectomy, secondary fasciectomy or dermofaciectomy following recurrent disease (p=0.5). A similar pathogenesis in both primary and recurrent disease is likely and nodularity is unlikely to be down-regulated following previous surgery. Indeed, the increased motion following initial surgery may facilitate myofibroblast differentiation and persistence. It is possible that residual unexcised Dupuytren's tissue following fasciotomy or fasciectomy and firebreak dermofasciectomy, may serve as a trigger for recurrence. The persistence of myofibroblasts may explain the high recurrence rates seen following surgical fasciotomy or collagenase injection. Therefore, a key element of preventing recurrent disease may be to down regulate the remaining myofibroblasts.

95% (36/38) of nodules were in the vicinity of the PIPJ and nodules were also observed over the MCPJ in the only two cases marked intra-operatively for the MCPJ and one case marked for the DIPJ. In early or active disease, tension may act intermittently on Dupuytren's tissue as active extension of the PIPJ offers resistance against the thickened, contracted palmar fascia. The increased tension sensed by cells may promote myofibroblast differentiation through recruitment of α-SMA to stress fibres and specialised attachment site formation under strict control of TGF-β1. This in turn leads to greater force generation. A densely packed cellular nodule could then theoretically exert sufficient force to promote or sustain digital contracture. The cells then remodel the surrounding matrix to a more shortened configuration. The resulting increased flexion deformity would impair function and the reduced movement at the joint would in turn lead to a reduction in tension sensed by nodular myofibroblasts. It is possible that with advanced digital contractures, reduced tension through limited active joint extension may lead to myofibroblast apoptosis, whereby myofibroblast rich nodules fail to persist. This may explain the progression from nodular to non-nodular cords and would also explain why patients with non-nodular cords tended to have more severe flexion deformities. Thus, myofibroblast aggregation in nodules in the vicinity of joints may lead to digital contracture and with subsequent matrix remodelling result in shortening of the affected fascia. Eventually fixed flexion deformity develops leading to an altered mechanical environment with loss of tension, myofibroblast apoptosis and thus may explain residual non-nodular cords. It can be concluded that the myofibroblast phenotype depends on tension in the surrounding matrix.

The culture force monitor (CFM) utilised and culture conditions are shown in FIGS. 3A to 3E: (A) Rectangular seeded collagen gels were cast and floated in medium, tethered between two flotation bars one of which is held stationary whilst the other is attached to a force transducer. (B) Cell-generated tensional forces in the collagen gel are detected by the force transducer, and live data are logged every 15 seconds providing a continuous output of force (dynes, $1 \times 10^5$ N) generated. (C) After 24 hour contraction, gels are harvested and processed for α-SMA mRNA, protein and immunofluorescence. (D) Cells were routinely seeded in gels with a high aspect-ratio collagen lattice, although low aspect-ratio lattices (E) were also used in experiments to compare effects of less strain on cell contractility.

Surgically excised cords were bisected and half processed for cell culture, whilst the cut surface of the mirror half was processed to identify samples with α-SMA-rich nodules (condensation of cells) by immunohistochemistry. Subsequent quantification by immunofluorescence demonstrated on average 35% of cells expressed α-SMA stress fibres in histology confirmed nodular samples, as compared to 10% α-SMA stress fibres in non-nodular samples. Although this still does not constitute a homogenous population of myofibroblasts, this method of sampling α-SMA-rich cells represents a significant improvement on previous studies, which have reported on average between 9.7% and 15% α-SMA-positive cells isolated from clinical and not histologically defined nodules. 1-4% of dermal fibroblasts were found to have α-SMA positive stress fibres.

FIGS. 4A to 4C show isometric contraction of collagen gels by dermal fibroblasts and Dupuytren's nodule-derived cells. Collagen gels were seeded with 1.5 million non-palmar fibroblasts (FIG. 4A), palmar fibroblasts (FIG. 4B) or Dupuytrens nodule-derived cells (FIG. 4C), cultured for 24 h in the CFM and real-time isometric force contraction was quantified. Data shown represent triplicate experiments using cells derived from one patient. Dermal fibroblasts in fibroblast populated collagen lattices (FPCL) in our CFM reached a plateau, whereas nodule-derived cells continued to contract in a dose-dependent manner over a 24 hour test period.

FIG. 5 shows that cells isolated from nodules had a much higher rate of contraction measured as the average rate of contraction between 6 and 24 hours in the CFM compared to palmar or non-palmar dermal fibroblasts. High contractility is one of the characteristics of myofibroblasts and is responsible for digital contracture in Dupuytren's disease.

In FIGS. 6A to 6E, it is shown that the contractility of Dupuytren's nodule-derived cells is regulated by post-transcriptional changes in α-SMA: (FIG. 6A) [rate of contraction (dynes/hr)] Isometric force in collagen gels with nodule-derived myofibroblasts (nodule), non-palmar (NPS) and palmar dermal fibroblasts (PS) over 24 hours (±SEM). After 24 h (FIG. 6B) α-SMA mRNA was compared to RPLPO by quantitative RT-per, (FIG. 6C) α-SMA mRNA compared to GAPDH and (FIG. 6D) α-SMA protein compared with vimentin. Experiments were performed in triplicate and data are shown as the mean (±SEM) from a total of 3 different nodular and non-nodular matched patient samples After harvesting FPCLs following 24 hours contraction in the CFM, comparisons were made between α-SMA mRNA levels, α-SMA protein expression and α-SMA protein localisation by immunofluorescence in the matched cell types. No differences in α-SMA mRNA levels were seen between nodule-derived cells and dermal fibroblasts, although approximately 3-fold greater α-SMA protein levels were seen in nodule-derived cells compared with matched dermal fibroblasts. Furthermore, using immunofluorescence we found that in dermal fibroblasts, α-SMA was typically distributed in a 'halo' within the peri-nuclear cytoplasm, whereas in nodule-derived cells, α-SMA was frequently localised in stress fibres throughout the cell processes up to cell-matrix attachment sites, as can be seen in FIG. 6E.

Cells were also cultured on glass coverslips for 24 hours, fixed and then immunofluorescently labelled using α-SMA antibodies (red), phalloidin (green) and DAPI (blue). Our immunofluoresence data demonstrate that palmar and non-palmar fibroblasts when cultured in monolayer acquired a proto-myofibroblast phenotype, with the expression of de novo cytosolic α-SMA. In contrast, significantly more differentiated myofibroblasts with α-SMA incorporated to stress fibres were seen in nodule-derived cells. These differences seen between nodule-derived, non-palmar and palmar skin cells from matched samples have not been previously reported. We simultaneously examined α-SMA protein levels, protein localization and mRNA levels in cells isolated from the same patient. Our findings suggest that post-transcriptional changes in α-SMA occur in genetically matched cells to mediate the Dupuytren's myofibroblast cell phenotype.

Example 2—Role of Inflammation in Dupuytren's Disease

The nodules were then examined for the presence of other cell types, specifically inflammatory cells. We found that large numbers of both macrophages and mast cells were present in nodules but not in non-nodular regions of the cords.

Figure 7A:
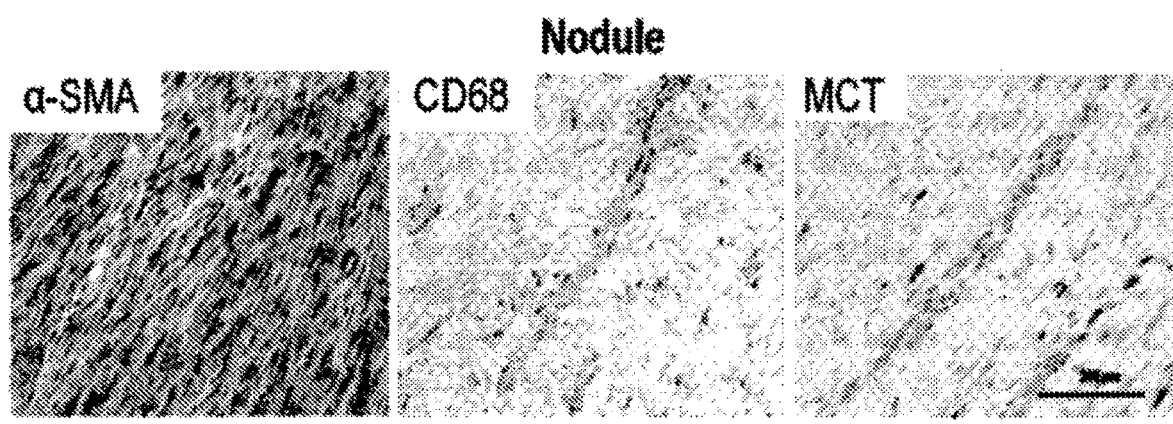
FIGS. 7A and 7B shows images of inflammatory cells (macrophages, CD68, mast cells, mast cell tryptase) in Dupuytren's nodule and cord.
Figure 7B:
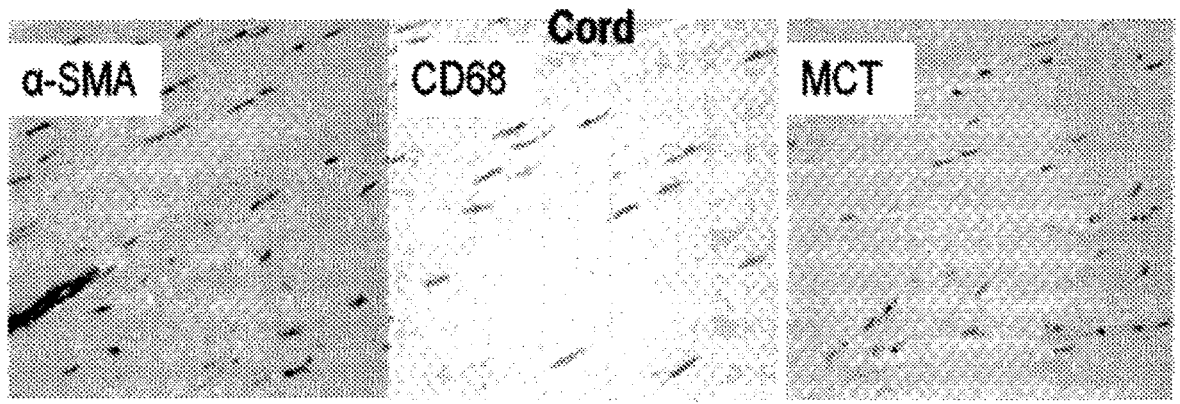

FIGS. 7A and 7B show inflammatory cells in Dupuytren's nodule and cord. Digital cord sections were serially stained for α-SMA, CD68 positive macrophages and mast cell tryptase. The images are representative of 15 patient samples.

We systematically quantified the number of inflammatory cells observed throughout excised Dupuytren's cord tissue in 10 patient samples. For each region (nodule, cord distal to nodule and non-nodular cord), the total number of cells, the number of α-SMA positive cells and cells stained for neutrophil elastase, mast cell tryptase, CD3 positive T cells, CD 4 positive T cells, CD68 positive macrophages were counted (×20 magnification) (Table 1).

TABLE 1

Quantification of total cell number: α-SMA positive cells, CD3 positive T cells, CD4 positive T cells, CD68 positive macrophages, and cells positive for mast cell tryptase and neutrophil elastase throughout excised Dupuytren's cord. Nodules, cord distal to nodule and non-nodular cord were analysed (presented as mean count (±SDEV) per mm$^2$) Six fields of view were counted within each region.

| IHC stain | Nodule | | Distal to nodule | | Non-nodular cord | |
|---|---|---|---|---|---|---|
| | mean | SDEV | mean | SDEV | mean | SDEV |
| Total cells | 1515 | 181 | 416 | 104 | 504 | 163 |
| α-SMA | 1493 | 199 | 12 | 8 | 8 | 7 |
| Neutrophil elastase | 2 | 1 | 0 | 1 | 0 | 0 |
| CD3 positive T cells | 220 | 99 | 2 | 2 | 1 | 2 |
| CD4 positive T cells | 2 | 1 | 0 | 0 | 0 | 0 |
| CD68 positive macrophages | 282 | 54 | 1 | 1 | 1 | 1 |
| Mast cell tryptase | 48 | 11 | 1 | 1 | 0 | 1 |

These data show that CD68 positive macrophages, CD3 T-cells and mast cell tryptase positive cells were common within cellular nodules and sparse within cord tissue. Neutrophil elastase positive cells and CD4 positive T-cells were observed infrequently throughout Dupuytren's tissue. Dupuytren's nodular tissue is populated with highly contractile myofibroblasts, the presence of inflammatory cells suggests that inflammation may be important in pathogenesis of the disease. In non-nodular cord, almost no inflammatory cells were observed and it is also of interest that virtually no cells stained positive for neutrophil elastase in either nodular or non-nodular cord. This is in contrast to inflammation during wound healing, where neutrophils are commonly seen and they are involved with clearance of debris and bacteria and initiating myofibroblast-dependent wound contraction. However, it is important to note that whilst excised digital cord samples contain nodules, they do not necessarily reflect the processes at the earliest stages of the disease.

Example 3—Advanced Glycation End Products and their Receptor

We examined the distribution of RAGE in Dupuytren's tissue and both palmar and non-palmar skin. We found abundant staining for RAGE in Dupuytren's nodules, where it co-localised with the myofibroblasts (see FIGS. 8A to 8D). Digital cord samples were longitudinally bisected and fixed in formalin. Histological sections were taken from the cut surface of cord and serial sections were stained for (FIG. 8A, FIG. 8C) α-SMA and (FIG. 8B, FIG. 8D) RAGE antibodies. Scale bars as shown. Images are representative from 15 patient samples. RAGE co-localises with α-SMA distribution in Dupuytren's nodules.

We also found increased staining for RAGE in the superficial layers of the epidermis in palmar skin compared to non-palmar skin and FACS staining showed significantly higher RAGE expression by dermal fibroblasts from palmar skin compared to non-palmar skin. See FIGS. 9A to 9D.

Non-palmar and palmar skin samples were fixed in formalin. Histological sections were stained for RAGE. (FIG. 9A, FIG. 9C) Non-palmar skin and (FIG. 9B, FIG. 9D) palmar skin. Scale bars are shown. Images are representative from 6 matched patient samples. FIGS. 9A to 9D illustrate the differential distribution of RAGE within non-palmar and palmar skin.

Figure 10A:
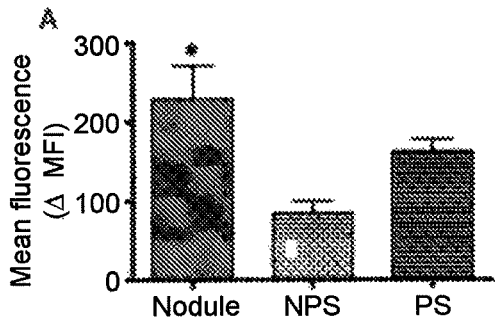
FIGS. 10A, 10B, 10C, 10D, 10E and 10F provide charts showing FACS analysis for cells deriving from nodular, non-palmar and palmar skin fibroblasts for expression of RAGE.
Figure 10B:
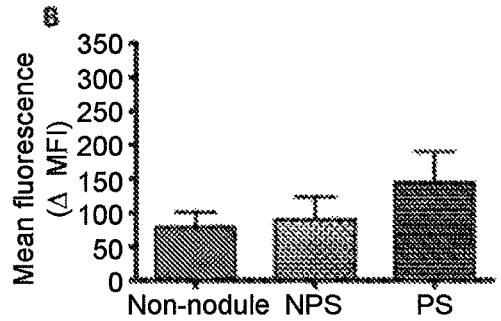
Figure 10C:
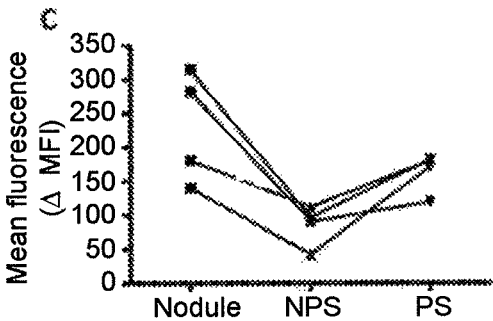
Figure 10D:
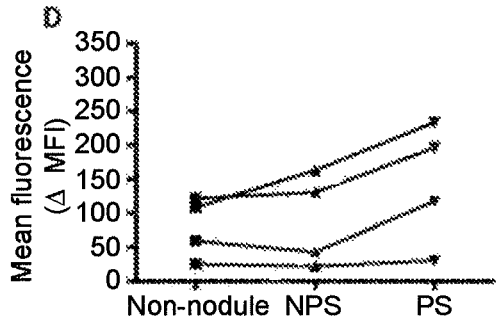
Figure 10E:
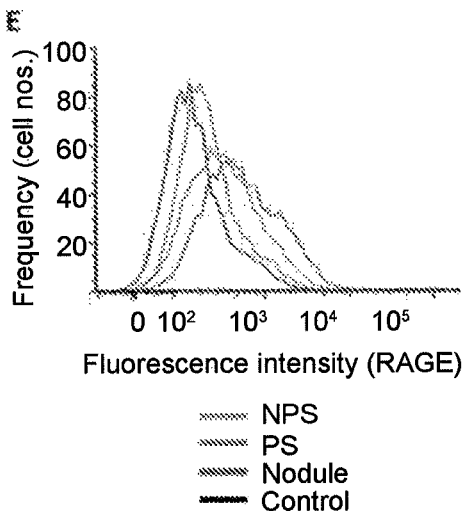
Figure 10F:
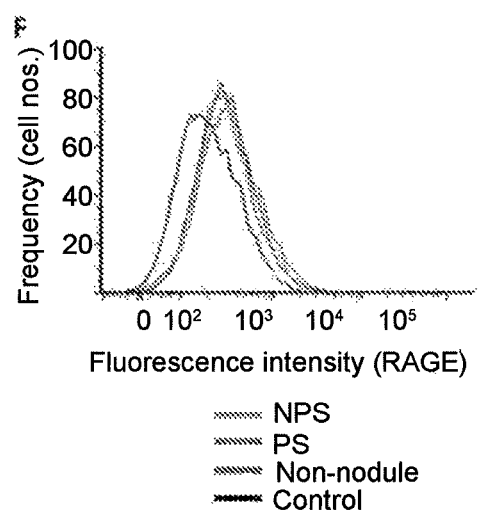

We also demonstrated that nodule-derived cells express higher levels of cell surface RAGE than matched dermal fibroblasts. Nodule-derived cells, palmar and non-palmar fibroblasts (1×10$^4$ cells per experiment) were stained with RAGE antibody, fluorescently labelled and mean fluorescence intensity assessed by FACS analysis. (FIG. 10A, FIG. 10C) Cell surface RAGE expression levels in nodule-derived cells as compared with matched dermal fibroblasts. (FIG. 10B, FIG. 10D) Cell surface RAGE expression levels in non-nodular cells as compared with matched dermal fibroblasts. Results in FIG. 10A and FIG. 10B are shown for 4 matched nodular patient and non-nodular samples (±SEM). *represents p=0.01. (FIG. 10E) RAGE fluorescent intensity trace showing nodule-derived cells, non-palmar fibroblasts, palmar fibroblasts and isotype control from 1 representative nodular matched patient sample, and (FIG. 10F) from 1 representative non-nodular matched patient sample. See FIGS. 10 A to 10F.

Figure 11:
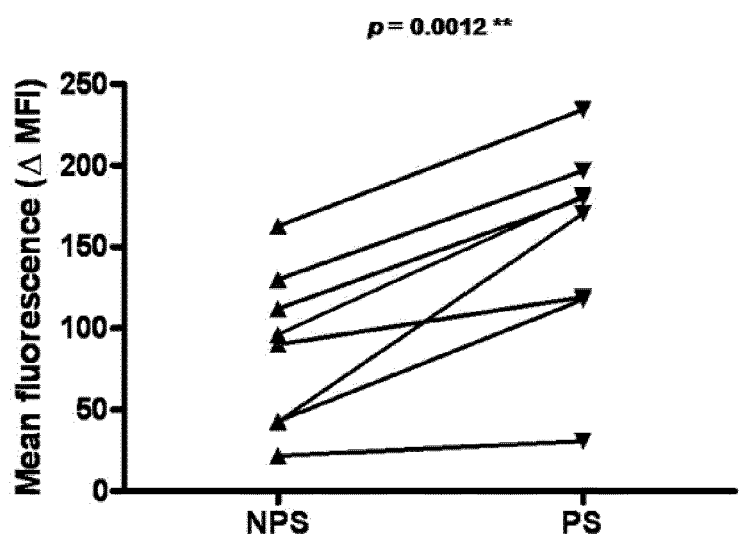
FIG. 11 provides charts showing FACS analysis for cells deriving from matched sets of non-palmar and palmar skin for expression of RAGE.

We demonstrated that RAGE cell surface expression is greater in palmar than non-palmar fibroblasts. Fibroblasts (1×10$^4$) from matched palmar and non-palmar skin were stained with RAGE antibody, fluorescently labelled and the mean fluorescence intensity analysed by FACS. Cell surface RAGE expression levels were consistently higher in palmar fibroblasts than non-palmar fibroblasts. Data are shown from 8 matched patient samples. See FIG. 11.

Figure 14:
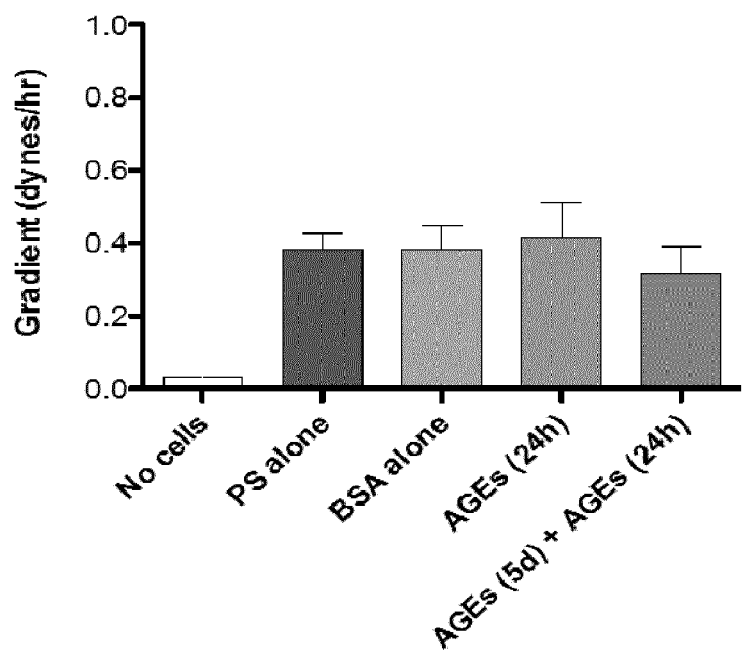
FIG. 14 is a chart showing the contractility of palmar dermal fibroblasts exposed to AGEs

In a further experiment to investigate the effect of AGE on myofibroblast formation, collagen gels were seeded with 1.5 million palmar fibroblasts and cultured for 24 h in the absence (PS alone) or presence of bovine serum albumin (BSA) (15 µg/ml), or AGEs-BSA (150 µg/ml) for varying periods and isometric force contraction quantified in the culture force monitor. Data are shown as +/−SEM from triplicate experiments with samples from 3 different patients in FIG. 14. It is apparent from FIG. 14 that contractility of palmar dermal fibroblasts is not affected by exposure to AGEs.

Figure 20:
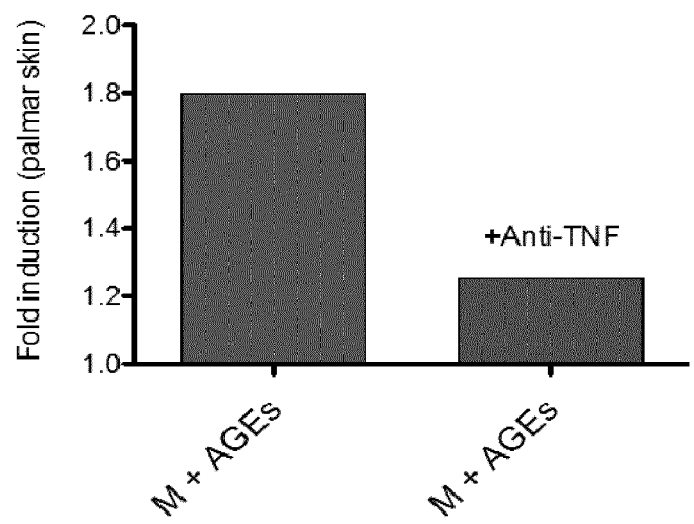
FIG. 20 is a chart of fold induction in contraction of palmar fibroblasts on exposure to supernatant from monocytes stimulated with AGEs, with or without anti-TNF-α.

We went on to investigate whether advanced glycation end products may also act via inflammatory cells and in other systems have been shown to lead to pro-inflammatory cytokine release (Uribarri et al., 2005). Collagen gels seeded with palmar fibroblasts were cultured for 24 h with supernatants from AGE-(100 µg/ml) stimulated monocytes (M) in the absence or presence of anti TNF-α (10 µg/ml) and isometric force contraction quantified. Experiments were performed in duplicate. Interestingly the supernatant from human monocytes co-cultured with AGEs stimulated palmar fibroblast contraction in a TNF-α dependent manner (FIG. 20).

Example 4

We examined the effect of addition of exogenous HMGB1 to palmar fibroblasts. Collagen gels seeded with palmar fibroblasts were cultured for 24 h in the absence (PS alone) or presence of TNF-α (1 ng/ml), or HMGB1 (1 ng/ml) or TGF-β1 (10 ng/ml) and isometric force contraction quantified (utilising the culture force monitor technique, such as described in Verjee et al, Hand Surg Am, 34, 1785-1794, 2009 and Verjee et al, J Cell Physiol, 2010). Data from the experiment are shown in FIG. 12 as +/−SD from triplicate experiments (except HMGB1 which is duplicate).

Figure 12:
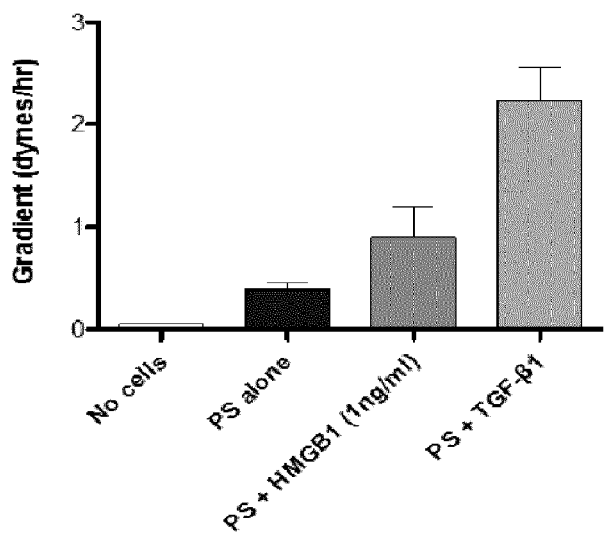
FIG. 12 provides a chart of contractility for palmar skin dermal fibroblasts treated with TNF-α, HMGB1 or TGF-β1.

Whilst there was a trend towards increased contraction resulting from HMGB1, this was not statistically significant (FIG. 12). Our data showed significant increased palmar fibroblast contractility (p=0.0001) with 10 ng/ml TGF-β1 compared to untreated palmar fibroblasts.

Figure 15:
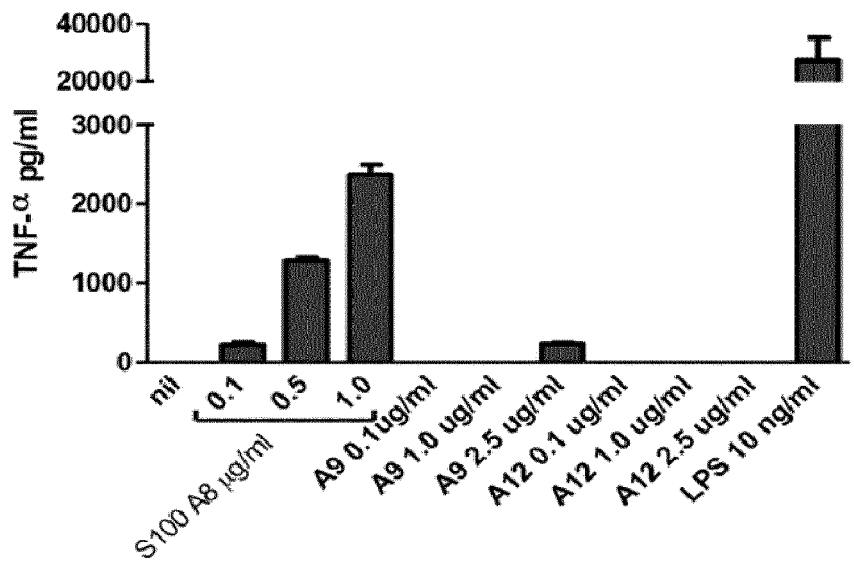
FIG. 15 is a chart showing TNF-α production from human monocytes exposed to certain DAMPs. LPS is a PAMP, shown as positive control.

We found that human monocytes exposed to S100A8 and to some extent S100A9 (other Alarmins) produced TNF-α in a dose dependent manner, as is illustrated by FIG. 15 As can be seen from FIG. 15, S100A8 is more active than S100A9 and S100A12 within the tested range. LPS, a pathogen associated molecular pattern (PAMP) is shown as positive control.

Figure 16:
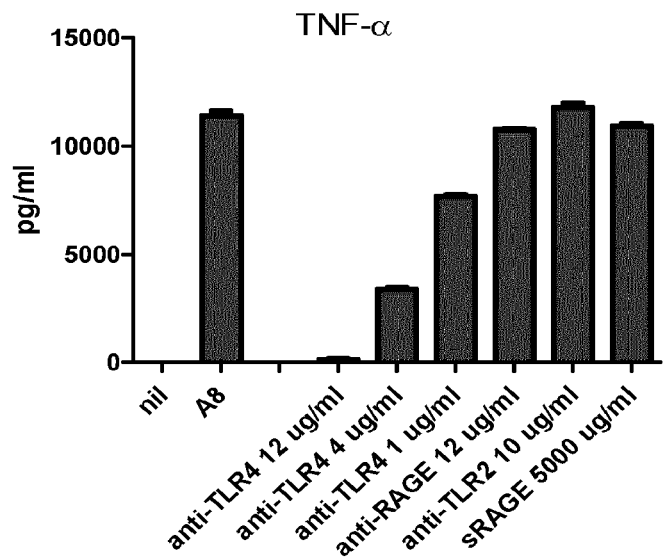
FIG. 16 is a chart showing TNF-α production from human monocytes exposed to certain DAMPs in the presence of certain receptor blockers.

The known receptors for S100A8 are the receptor for advanced glycation end products (RAGE) and the Toll-like receptors 2 and 4. Human monocytes at $1\times10^5$/ml were incubated in 10% FCS with human S100 A8 at 0.5 with the addition of either antibody to TLR4, TLR2 or isotype controls (not shown), or soluble RAGE (sRAGE)) over 14 hours. TNF-α levels were determined by ELISA. We have found that the predominant receptor for binding S100A8 on monocytes leading to TNF-α production is TLR-4 and not RAGE or TLR-2 (FIG. 16).

Figure 17:
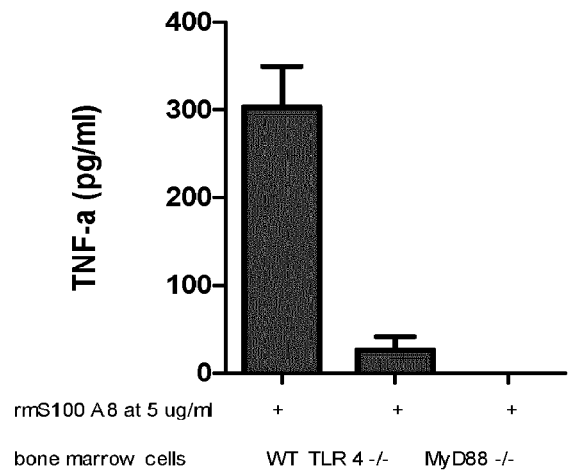
FIG. 17 is a chart showing TNF-α production from murine bone marrow cells in the presence of S100 A8 in turn in cells having TLR-4 deficiency and MyD88 deficiency.

We have confirmed that S100A8 predominantly binds to TLR-4 and that the intracellular signalling leading to TNF-α production by monocytes is entirely dependent on adaptor protein MyD88 by comparing the effect of murine S100A8 on TNF-α production by bone marrow cells derived from TLR-4 or MyD88 deficient mice with bone marrow derived cells from wild-type C57Bl/6 animals (FIG. 17). In FIG. 17, TNF-α produced by murine bone marrow cells of wild type, TLR4$^{-/-}$ and MyD88$^{-/-}$ mice on exposure to murine S100A8 were measured by ELISA.

Figure 18:
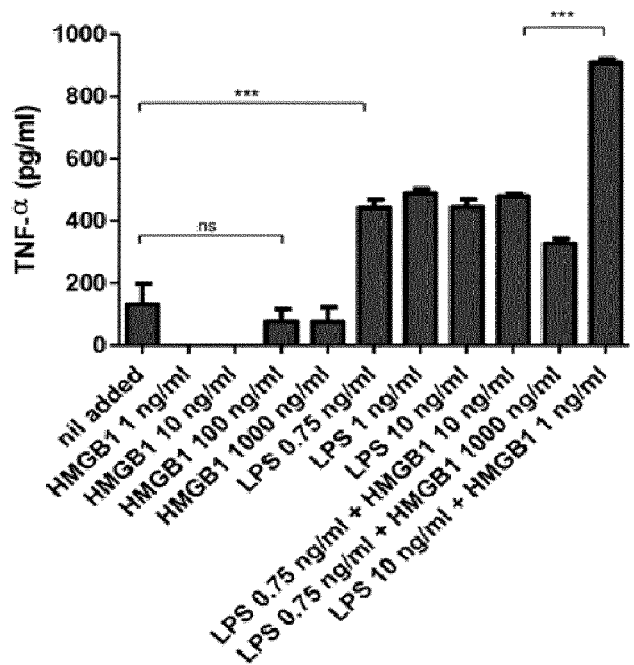
FIG. 18 is a chart showing TNF-α production from human monocytes exposed to a certain DAMP alone and in combination with LPS.

It is more difficult to show in vitro that HMGB1 also acts on monocytes to lead to pro-inflammatory cytokine release. This is because in vivo it acts in conjunction with other TLR ligands and highly purified HMGB1 alone does not lead to TNF-α production by monocytes in vitro (FIG. 18). Our experiment, the results of which are shown in FIG. 18, involved human monocytes at $1\times10^5$/ml incubated in 10% FCS with HMGB1 or LPS alone or together at concentrations shown over 14 hours. TNF-α levels were determined by ELISA. It was found that HMGB1 alone does not stimulate TNF-α production by monocytes but is active in combination with LPS.

Figure 19:
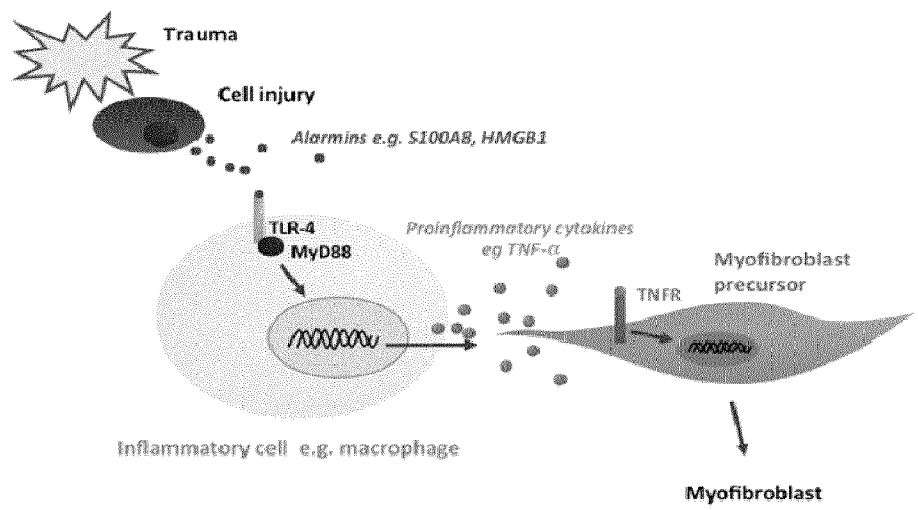
FIG. 19 is a schematic of proposed mechanism of the role of trauma and Alarmins in the pathogenesis of Dupuytren's disease.

FIG. 19 shows a schematic of proposed mechanism of the role of trauma and alarmins in the pathogenesis of Dupuytren's disease. As can be seen, trauma (101) causes cell injury (103) and consequent release of Alarmins (105) such as S100A8, which binds to TLR-4 (107) in an inflammatory cell such as a macrophage (109) causing pro-inflammatory cytokines such as TNF-α to be produced (113) signalled via Myd88 (111). TNF-α may then bind to TNFR (115) on fibroblast precursor (117) resulting in formation of myofibroblast (119).

Example 5

Figure 13:
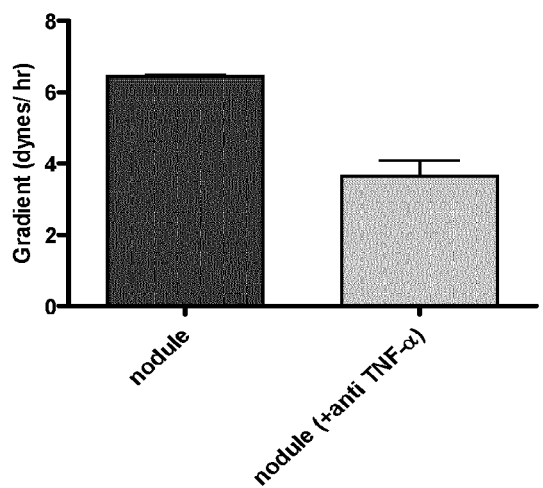
FIG. 13 is a chart showing the contractility of primary passage nodule-derived cells (from a Dupuytren's patient) and in the presence or absence of anti-TNF-α.

Primary passage cultured cells from a Dupuytren's nodule (comprising myofibroblast cells) were treated, using the culture force monitor described above, with a monoclonal human TNF-α antibody (monoclonal IgG$_1$ culture #1825, as available from R&D Systems of Canada) in an amount of 10 µg/ml. Compared with a control culture of such primary passage cells, the anti-TNF-α treated cells were found over 24 hours to contract by an amount of greater than 30% less than control (which it is believed corresponds to effective myofibroblast deactivation of greater than 30% compared with control). This is shown in FIG. 13, where the gradient (or rate of contraction; in Dynes/h) over 24 hours is illustrated for each of the control cells and the TNF-α antibody treated cells.

This directly shows that myofibroblast cells cultured from a clinical from a Dupuytren's disease patient has reduced activity (e.g. reduced contractile behaviour and/or reduced abundance) when treated with a TNF-α antagonist, even over only 24 hours. Since the effect of the TNF-α antagonist on myofibroblasts in the clinical situation will be ongoing and the therapeutic regime in a patient may involve repeat applications, it is believed that this experiment shows that myofibroblast activity can be effectively managed, thereby reducing the progression of and/or inhibiting the recurrence of musculoskeletal fibroproliferative disorders and, in particular, Dupuytren's disease by local application of a TNF-α antagonist to the disease site.

Figure 21:
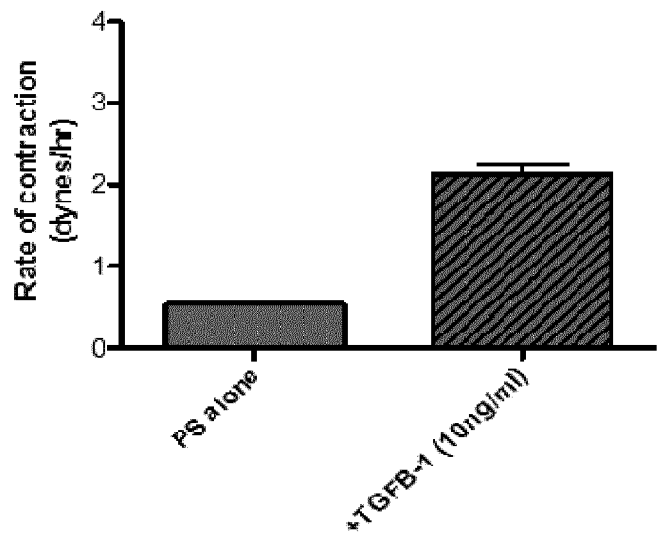
FIG. 21 is a chart showing the contractility of palmar dermal fibroblasts and dose response to TGF-β1.

We were able to confirm that addition of TGF-β1 human palmar fibroblasts from in a collagen lattice under isometric conditions enhanced contractility (see FIG. 21). Collagen gels seeded with palmar fibroblasts were cultured for 24 h in the absence (PS alone) or presence of TGF-β1 (long/ml). Data are shown as +/−SD from triplicate experiments using cells from 3 patients.

Figure 22:
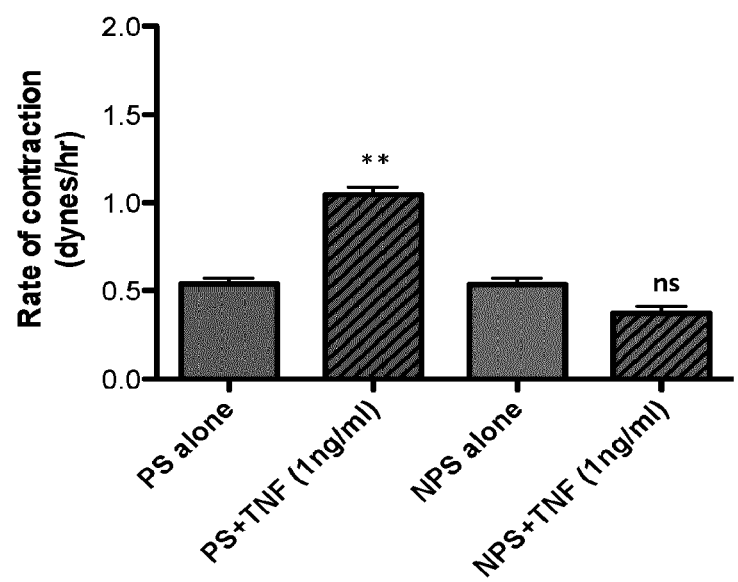
FIG. 22 is a chart showing that palamar dermal fibroblasts from patients with Dupuytren's disease exposed to TNF-α become more contractile whereas non-palmar dermal fibroblasts do not.

We then compared the effect of TNF-α on the rate of contraction on palmar skin and non-palmar skin from a Dupuytren's patient. Collagen gels seeded with palmar fibroblasts were cultured for 24 h in the absence (PS or NPS alone) or presence of TNF-α (1 ng/ml). Data are shown as +/−SD from triplicate experiments using cells from 3 patients for palmar skin and one patient non-palmar skin (**p=0.0012, ns=not significant). We found significantly enhanced contraction in the culture force monitor (FIG. 22) on addition of TNF-α to the palmar skin fibroblasts. However, there was no change, or a slight reduction, in contraction rate when TNF-α was added to non-palmar dermal fibroblasts also obtained from patients undergoing dermofasciectomy for Dupuytren's disease. It is interesting to note that Dupuytren's disease only affects the palms of the hand and rarely the soles of the feet or the tunica albuginea of the penis (Peyronie's disease).

Figure 23:
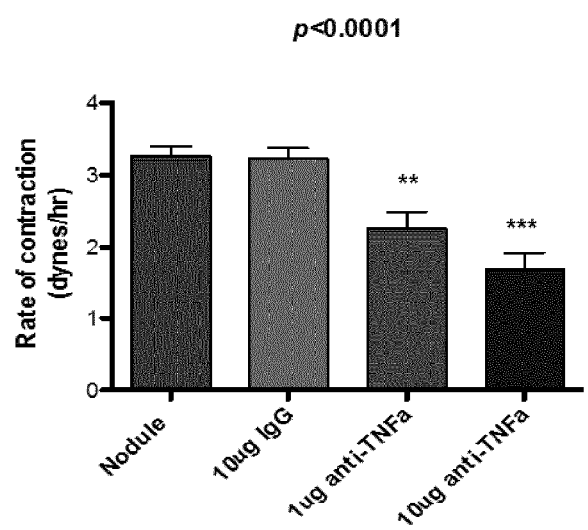
FIG. 23 is a chart showing a dose related inhibition of contractility of cells form Dupuytren's nodules exposed to TNF-α antagonist.

The key next question was whether the contractility of myofibroblasts in Dupuytren's disease could be reversed by the addition of anti-TNF-α in a dose-dependent manner. Collagen gels seeded with 1.5 million Dupuytren's myofibroblasts/fibroblasts were cultured for 24 h in the presence of anti TNF-α (murine anti-human R&D Systems, MAB2010) and isometric force contraction quantified. Experiments were performed in triplicate using cells from 5 consecutive unselected patients. There was no effect with isotype control antibody or with 0.1 μg/ml of anti TNF-α. Values represent mean±SEM. The results are shown in FIG. 23. Addition of anti-TNF-α at a dose range of 1-10 μg/ml to myofibroblasts from Dupuytren's cord down-regulated their contraction in the culture force monitor in a dose-dependent manner (FIG. 23).

Figure 24A:
FIG. 24A is an image showing cells from a Dupuytren's nodule in a 3-dimensional collagen gel exposed only to control IgG antibody stained with phalloidin and exhibiting alignment in axis of stress.

We next assessed the effect of anti-TNF-α on myofibroblast morphology. All the cells in the untreated gels or those exposed to IgG isotype control antibody were spindle shaped and aligned in the axis of maximal stress (FIG. 24a). However, in the gels treated with 10 μg/ml anti-TNF-α, many of the cells showed a stellate morphology, without any alignment to the direction of stress (FIG. 24b,c).

Figure 24B:
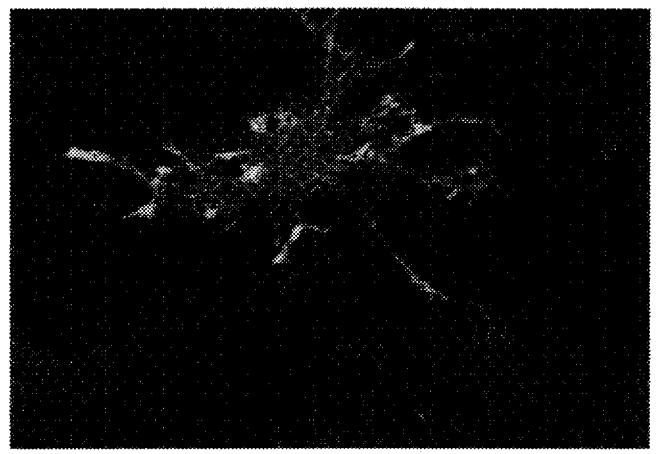
FIGS. 24B and 24C are images showing cells from a Dupuytren's nodule stained with phalloidin and α-SMA respectively, treated with a TNF-α antagonist, showing loss of alignment in axis of stress.
Figure 24C:

For the experiments for FIGS. 24A to 24C, gels from the experiments shown in FIG. 23 were fixed in 3% paraformaldehyde were immunofluorescently labelled using α-smooth muscle actin antibodies (red), phalloidin (green) and DAPI (nuclei-blue). FIG. 24A shows cells from a gel exposed to isotype control IgG antibody. FIGS. 24B and 24C show cells from a gel exposed to 10 μg/ml anti-TNF-α antibody stained with phalloidin and antibody to α-smooth muscle actin respectively. Original images photographed at ×100.

Figure 25:
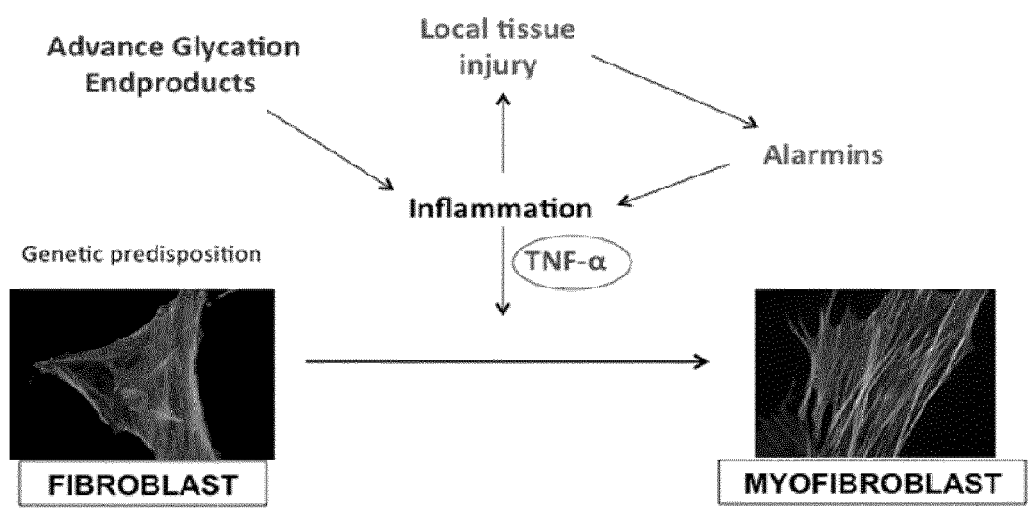
FIG. 25 is a schematic of a proposed role of advanced glycation end products, injury and alarmins in the pathogenesis of fibroproliferative disorders, highlighting the key role of TNF-α in the final common pathway.

FIG. 25 illustrates a schematic of proposed role of advanced glycation end products, injury and alarmins in the pathogenesis of fibroproliferative disorders, highlighting the key role of TNF-α in the final common pathway. Hence TNF-α is a key therapeutic target for both early Dupuytren's disease and to prevent recurrence following treatment with collagenase.

These Examples illustrate initial findings that enhance understanding of Duputren's nodule material and contractile behaviour especially relating to the role and behaviour of active myofibroblasts. These findings implicate TNF-α in myofibroblast activity as well as DAMPS and AGE, which support the finding that TNF-α antagonists, DAMP antagonists and/or AGE inhibitors may be used to prevent or inhibit disease onset or progression from early state disease to established state disease and to prevent or inhibit disease recurrence in established disease where patients have undergone a primary corrective treatment.

The invention has been described with reference to a preferred embodiment. However, it will be appreciated that variations and modifications can be effected by a person of ordinary skill in the art without departing from the scope of the invention.

The invention claimed is:

1. A method for treating a patient with early disease state periarticular fibrosis or adhesion comprising injecting an amount of a TNF-α antagonist effective to treat the patient directly at the site of the early disease state periarticular fibrosis or adhesion, so as to treat the patient.

2. A method of claim 1, wherein the TNF-α antagonist is selected from one or more of Infliximab, Adalimumab, Certolizumab pegol, Golimumab or Etanercept.

3. A method of claim 1, wherein the TNF-α antagonist is an anti-TNF-α antibody.

4. A method of claim 1, wherein the TNF-α antagonist is Infliximab.

5. A method of claim 1, wherein the TNF-α antagonist is Adalimumab.

6. A method of claim 1, wherein the TNF-α antagonist is Certolizumab pegol.

7. A method of claim 1, wherein the TNF-α antagonist is Golimumab.

8. A method of claim 1, wherein the TNF-α antagonist is Etanercept.

9. A method of claim 1 further comprising administering an extracellular matrix degradation, depletion or cleavage agent.

10. A method of claim 9, wherein the extracellular matrix degradation, depletion or cleavage agent is a matrix metalloproteinase and/or a collagenase.

11. A method of claim 9, wherein the extracellular matrix degradation, depletion or cleavage agent is administered locally to the disease site.

* * * * *